US008883120B2

(12) United States Patent
Abrahmsén et al.

(10) Patent No.: US 8,883,120 B2
(45) Date of Patent: Nov. 11, 2014

(54) POLYPEPTIDES HAVING AFFINITY FOR HER2

(71) Applicant: Affibody AB, Solna (SE)

(72) Inventors: Lars Abrahmsén, Bromma (SE); Nina Herne, Stockholm (SE); Joachim Feldwisch, Tyresö (SE); Christofer Lendel, Farsta (SE); Vladimir Tolmachev, Uppsala (SE)

(73) Assignee: Affibody AB, Solna (SE)

( * ) Notice: Subject to any disclaimer, the term of this patent is extended or adjusted under 35 U.S.C. 154(b) by 0 days.

(21) Appl. No.: 13/928,522

(22) Filed: Jun. 27, 2013

(65) Prior Publication Data

US 2013/0280164 A1    Oct. 24, 2013

Related U.S. Application Data

(62) Division of application No. 12/735,068, filed as application No. PCT/EP2008/068167 on Dec. 22, 2008, now Pat. No. 8,501,909.

(30) Foreign Application Priority Data

Dec. 21, 2007  (EP) ................................. 07150395

(51) Int. Cl.
  *A61K 51/08*    (2006.01)
  *A61K 38/00*    (2006.01)
(52) U.S. Cl.
  USPC ................... 424/1.69; 514/19.3; 514/19.4
(58) Field of Classification Search
  None
  See application file for complete search history.

(56) References Cited

U.S. PATENT DOCUMENTS

| 7,993,650 | B2 * | 8/2011 | Carlsson et al. ........... 424/185.1 |
| 2009/0180954 | A1 | 7/2009 | Marino et al. | |
| 2009/0191124 | A1 | 7/2009 | Marino et al. | |

FOREIGN PATENT DOCUMENTS

| EP | 2 077 272 A1 | 7/2009 |
| WO | WO 91/01743 | 2/1991 |
| WO | WO 92/00091 | 1/1992 |
| WO | WO 95/19374 | 7/1995 |
| WO | WO2005/003156 | 1/2005 |
| WO | WO 2005/003156 | 1/2005 |
| WO | WO 2007/065635 | 6/2007 |
| WO | WO 2009/077175 A1 | 6/2009 |
| WO | WO 2009/077569 A1 | 6/2009 |
| WO | WO 2009/080811 A1 | 7/2009 |

OTHER PUBLICATIONS

Orlova, Anna et al., "*Tumor Imaging Using a Picomolar Affinity HER2 Binding Affibody Molecule*", Cancer Research, vol. 66, No. 8., pp. 4339-4348 (Apr. 15, 2006).
Wikman, M. et al., *Election and characterization of HER2/neu-binding affibody ligands*, Protein Engineering, Design & Selection, vol. 17, No. 5, pp. 455-462 (Jun. 18, 2004).
Orlova, Anna et al., "*Affibody Molecules for Molecular Imaging and Therapy for Cancer*", Cancer Biotherapy & Radiopharmaceuticals, vol. 22, No. 6, pp. 573-584 (2007).
Orlova, Anna et al., "*Synthetic Affibody Molecules: A Novel Class of Affinity Ligands for Molecular Imaging of HER2-Expressing Malignant Tumors*", Cancer Research, vol. 67, No. 5, pp. 2178-2186 (Mar. 1, 2007).
Tran, Thuy et al., "$^{99m}Tc$-$maEEE$-$Z_{HER2:342}$, *an Affibody Molecule-Based Tracer for the Detection of HER2 Expression in Malignant Tumors*", Bioconjugate Chemistry, vol. 18, No. 6, pp. 1956-1964 (2007).
Tolmachev, Vladimir et al., "*Radionuclide Therapy of HER2-Positive Microxenografts Using a$^{177}Lu$-Labeled HER2-Specific Affibody Molecule*", Cancer Research, vol. 67, No. 6, (Mar. 15, 2007).
Linhult, Martin et al., "*Improving the Tolerance of a Protein A Analogue to Repeated Alkaline Exposures Using a Bypass Mutagenesis Approach*", Proteins, vol. 55, pp. 407-416 (2004).

* cited by examiner

*Primary Examiner* — Laura B Goddard
(74) *Attorney, Agent, or Firm* — Cantor Colburn LLP

(57) ABSTRACT

HER2 binding polypeptides comprising the amino acid sequence EX$_1$ RNAYWEIA LLPNLTNQQK RAFIRK-LYDD PSQSSELLX$_2$E AKKLNDSQ wherein X$_1$ in position 2 is M, I or L, and X$_2$ in position 39 is S or C (SEQ ID NO:1) are disclosed. Moreover, such peptides comprising a chelating environment are disclosed. Also radiolabeled polypeptides formed by the peptides comprising a chelating environment and radionuclides are disclosed. Furthermore, methods of in vivo imaging of the body of a mammalian subject having or suspected of having a cancer characterized by overexpression of HER2 comprising administration of such a radiolabeled polypeptide followed by obtainment of an image of the body using a medical imaging instrument and also methods of treating such cancer are disclosed. Furthermore, the use of such a radiolabeled polypeptide in diagnosis and treatment of cancer characterized by overexpression of HER2. Nucleic acids encoding the polypeptides, expression vectors comprising the nucleic acids and host cells comprising the expression vectors are also disclosed.

22 Claims, 18 Drawing Sheets

POLYPEPTIDES HAVING AFFINITY FOR HER2

CROSS-REFERENCE TO RELATED APPLICATIONS

This application is a Divisional of U.S. application Ser. No. 12/735,068 filed Oct. 6, 2010, which is a US National Stage Application of International Patent Application No. PCT/EP2008/068167 filed Dec. 22, 2008. All these applications are incorporated by reference in their entireties.

FIELD OF THE INVENTION

The present invention is related to new polypeptides which bind to Human Epidermal Growth Factor Receptor 2 (in the following referred to as HER2). The present invention also relates to use of such a HER2 binding polypeptide as a diagnostic agent and/or medicament, more particularly use thereof as a diagnostic agent and/or medicament for diagnosis and/or treatment of forms of cancer characterized by overexpression of HER2.

BACKGROUND

HER2 and its Role in Cancer Diseases

The HER2 proto-oncogene encodes the production of a 185 kDa cell surface receptor protein known as the HER2 protein or receptor (Hynes N E et al (1994) Biochim Biophys Acta 1198:165-184). This gene is also sometimes referred to as neu, HER2/neu or c-erbB-2. Neu was first discovered in rats that had been treated with ethylnitrosourea, and exhibited mutation of this gene (Shih C et al (1981) Nature 290:261-264). The mutated version of neu results in the production of a constitutively active form of the receptor, and constitutes a potent oncogene that can transform cells at low copy number (Hynes N E et al, supra).

Normal cells express a small amount of HER2 protein on their plasma membranes in a tissue-specific pattern. No known ligand to HER2 has been elucidated; however, HER2 has been shown to form heterodimers with HER1 (the epidermal growth factor receptor, EGFR), HER3 and HER4 in complex with the ligands for these receptors. Such heterodimer formation leads to the activated HER2 receptor transmitting growth signals from outside the cell to the nucleus, thus controlling aspects of normal cell growth and division (Sundaresan S et al (1999) Curr Oncol Rep 1:16-22).

In tumor cells, errors in the DNA replication system may result in the existence of multiple copies of a gene on a single chromosome, which is a phenomenon known as gene amplification. Amplification of the HER2 gene leads to an increased transcription of this gene. This elevates HER2 mRNA levels and increases the concomitant synthesis of HER2 protein, which results in HER2 protein over-expression on the surface of these tumor cells. This overexpression can result in HER2 protein levels that are 10- to 100-fold greater than those found in the adjacent normal cells. This, in turn, results in increased cell division and a concomitantly higher rate of cell growth. Amplification of the HER2 gene is implicated in transformation of normal cells to the cancer phenotype (Hynes N E et al, supra; Sundaresan S et al, supra).

Overexpression of HER2 protein is thought to result in the formation of homodimers of HER2, which in turn results in a constitutively active receptor (Sliwkowski M X et al (1999) Semin Oncol 26(4 Suppl 12):60-70). Under these conditions, growth-promoting signals may be continuously transmitted into the cells in the absence of ligands. Consequently, multiple intracellular signal transduction pathways become activated, resulting in unregulated cell growth and, in some instances, oncogenic transformation (Hynes N E et al, supra). Thus, the signal transduction mechanisms mediated by growth factor receptors are important targets for inhibiting cell replication and tumor growth.

Breast cancer is the most common malignancy among women in the United States, with 192200 new cases projected to have occurred in 2001 (Greenlee R et al (2001) CA Cancer J Clin 51:15-36). In approximately 25 of all breast cancer patients, there is an overexpression of the HER2 gene due to amplification thereof (Slamon D J et al (1989) Science 244: 707-712). This overexpression of HER2 protein correlates with several negative prognostic variables, including estrogen receptor-negative status, high S-phase fraction, positive nodal status, mutated p53, and high nuclear grade (Sjogren S et al (1998) J Clin Oncol 16(2):462-469). According to Slamon et al (supra), the amplification of the HER2 gene was found to correlate strongly with shortened disease-free survival and shortened overall survival of node-positive patients.

For these reasons, it has been, and is still, an important goal to further pursue investigations into the role of HER2 in the pathogenesis and treatment of breast cancer. The identification of molecules that interact with HER2 forms one part of this effort.

Preclinical in vitro studies have examined whether inhibition of HER2 activity could affect tumor cell growth. Treatment of SK-BR-3 breast cancer cells overexpressing HER2 protein with 4D5, one of several murine anti-HER2 monoclonal antibodies, did indeed inhibit tumor cell proliferation, compared with treatment with a control monoclonal antibody. Administration of 4D5 to mice bearing human breast and ovarian cancers (xenografts) that overexpress HER2 prolonged their tumor-free survival time. Similar studies demonstrated the growth inhibition by anti-HER2 monoclonal antibodies in human gastric cancer xenografts in mice (Pietras R J et al (1994) Oncogene 9:1829-1838).

Among the approaches to inhibiting the HER2 protein abundantly present on tumor cell surfaces with an antibody, one therapy has become commercially available during recent years. Thus, the humanized variant of monoclonal antibody 4D5, or trastuzumab, is marketed for this purpose by F Hoffman-La Roche and Genentech under the trade name of Herceptin®.

Overexpression of HER2 has thus been described for breast cancer. It has also been connected to i.a. ovarian cancer, stomach cancer, bladder cancer, salivary cancer, lung cancer (Holbro et al., Annu. Rev. Pharmacol. Toxicol. 2004. 44:195-217) and cancer in the esophagus (Ekman et al., Oncologist 2007; 12; 1165-1177, see in particular pages 1170-1171).

Notwithstanding the obvious advantages shown by antibody therapy against cancers characterized by overexpression of HER2 protein, the fact remains that a variety of factors have the potential of reducing antibody efficacy (see e.g. Reilly R M et al (1995) Clin Pharmacokinet 28:126-142). These include the following: (1) limited penetration of the antibody into a large solid tumor or into vital regions such as the brain; (2) reduced extravasation of antibodies into target sites owing to decreased vascular permeability; (3) cross-reactivity and nonspecific binding of antibody to normal tissues, reducing the targeting effect; (4) heterogeneous tumor uptake resulting in untreated zones; (5) increased metabolism of injected antibodies, reducing therapeutic effects; and (6) rapid formation of HAMA and human antihuman antibodies, inactivating the therapeutic antibody.

In addition, toxic effects have been a major obstacle in the development of therapeutic antibodies for cancer (Carter P (2001) Nat Rev Cancer 1:118-129; Goldenberg D M (2002) J Nucl Med 43:693-713; Reichert J M (2002) Curr Opin Mol Ther 4:110-118). Cross-reactivity with healthy tissues can cause substantial side effects for unconjugated (naked) antibodies, which side effects may be enhanced upon conjugation of the antibodies with toxins or radioisotopes. Immune-mediated complications include dyspnoea from pulmonary toxic effects, occasional central and peripheral nervous system complications, and decreased liver and renal function. On occasion, unexpected toxic complications can be seen, such as the cardiotoxic effects associated with the HER2 targeting antibody trastuzumab (Schneider J W et al (2002) Semin Oncol 29(3 suppl 11):22-28). Radioimmunotherapy with isotope-conjugated antibodies also can cause bone marrow suppression.

Despite the recent clinical and commercial success of the currently used anticancer antibodies, a substantial number of important questions thus remain concerning the future of the use of antibodies. As a consequence, the continued provision of agents with a comparable affinity for HER2 remains a matter of substantial interest within the field, as well as the provision of uses of such molecules in the diagnosis and treatment of disease.

HER2 Binding Z Variant Molecules

Molecules related to protein Z, derived from domain B of staphylococcal protein A (SPA) (Nilsson B et al (1987) Protein Engineering 1, 107-133), have been selected from a library of randomized such molecules using different interaction targets (see e.g. WO95/19374; Nord K et al (1997) Nature Biotechnology 15, 772-777; WO2005/000883; WO2005/075507; WO2006/092338; WO2007/065635).

In WO2005/003156, a substantial number of Z variants with an ability to interact with HER2 is disclosed.

DISCLOSURE OF THE INVENTION

It is an object of the present invention to satisfy the requirements of a continued provision of agents with an affinity for HER2, through the provision of a polypeptide that is characterized by specific binding to HER2.

A related object of the invention is an HER2 binding polypeptide which exhibits little or no non-specific binding.

It is another object of the invention to provide an HER2 binding polypeptide that can readily be used as a moiety in a fusion polypeptide.

Another object is the provision of an HER2 binding polypeptide, which solves one or more of the known problems experienced with existing antibody reagents.

A further object of the invention is to provide an HER2 binding polypeptide, which is amenable to use in therapeutic applications.

A further object of the invention is to provide an HER2 binding polypeptide, which is amenable to use in diagnostic applications.

A related object is to find new forms for the treatment, inhibition and/or targeting in the clinical setting of cancer diseases characterized by an overexpression of HER2 protein.

It is another object of the invention to provide an HER2 binding polypeptide which is easily synthesized by chemical peptide synthesis.

A related object is to find an HER2 binding polypeptide that exhibits an improved stability vis-á-vis known HER2 binding agents.

Yet another object of the invention is to achieve an HER2 binding polypeptide that exhibits a low antigenicity when used in vivo in a mammal.

It is another object of the invention to provide an HER2 binding polypeptide with an improved biodistribution upon administration to a mammal.

These and other objects are met by the different aspects of the invention as claimed in the appended claims. Thus, in a first aspect, the invention provides a polypeptide, which has an amino acid sequence that comprises

```
                                                              (SEQ ID NO: 1)
EX₁RNAYWEIA LLPNLTNQQK RAFIRKLYDD PSQSSELLX₂E AKKLNDSQ,
wherein X₁ in position 2 is M, I or L, and X₂ in position 39 is S or C
``` or in some cases more preferably

```
                                                              (SEQ ID NO: 2)
YAKEX₁RNAYW EIALLPNLTN QQKRAFIRKL YDDPSQSSEL

LX₂EAKKLNDS Q
wherein X₁ in position 5 is M, I or L, and X₂ in position 42 is S or C
``` or in some cases more preferably

```
                                                              (SEQ ID NO: 3)
AEAKYAKEX₁R NAYWEIALLP NLTNQQKRAF IRKLYDDPSQ

SSELLX₂EAKK LNDSQ,
wherein X₁ in position 9 is M, I or L, and X₂ in position 46 is S or C
``` or in some cases more preferably (SEQ ID NO: 4)

```
-continued
ESEKYAKEX₁R NAYWEIALLP NLTNQQKRAF IRKLYDDPSQ

SSELLX₂EAKK LNDSQ,
wherein X₁ in position 9 is M, I or L, and X₂ in position 46 is S or C
```

In accordance herewith, the present inventors have found that a polypeptide comprising any of the sequences SEQ ID NO: 1-4 exhibits surprising advantages, for example in comparison with the HER2 binding polypeptides disclosed in WO2005/003156, while retaining the capacity of those previously described polypeptides to bind the target HER2. Non-limiting examples of such advantages, exhibited by one or more embodiments of the polypeptide according to the invention, are as follows:

- The inventive polypeptide comprises fewer amino acid residues that could cause problems, such as low yield and success rate, in chemical synthesis of the polypeptide sequence, such as asparagine, arginine, aspartic acid and methionine.
- The inventive polypeptide comprises fewer amino acid residues that confer surface hydrophobicity, and thus has a more hydrophilic profile than previously described, related HER2 binding polypeptides. This implies fewer problems with low solubility and aggregation. Without wishing to be bound by theory, it is also currently believed that the more hydrophilic characteristics act to shift the biodistribution of the polypeptide upon administration to a host, from a hepatobiliary pathway (excretion through the liver) towards a more desired renal pathway (excretion through the kidneys).
- The inventive polypeptide comprises fewer amino acid residues that are associated with stability problems of polypeptides, such as methionine, asparagine and the dipeptide asparagine-proline. Methionine is susceptible to oxidation, asparagine is susceptible to deamidation and the asparagine-proline bond is susceptible to cleavage, and they therefore contribute to the non-homogeneity of the final product.
- The inventive polypeptide lacks amino acid residues that, in a similar sequence context, have been found to increase the interaction with immunoglobulins containing a heavy chain variable domain from VH3 (Silverman G. J., Int. Rev. Immunol. 1992; 9(1):57-78). Without wishing to be bound by theory, it is currently believed that the replacement of such amino acid residues in the polypeptides according to the invention reduces the antigenicity of the polypeptide upon administration of same to a host.

The inventive polypeptide finds application as an alternative to antibodies against HER2 in diverse applications. As non-limiting examples, they are useful in the treatment of cancers characterized by HER2 overexpression, in inhibiting cell signaling by binding to the HER2 on a cell surface, in the diagnosis of cancers characterized by HER2 overexpression both in vivo and in vitro, in targeting of agents to cells overexpressing HER2, in histochemical methods for the detection of HER2, in methods of separation and other applications. The polypeptide according to the invention may prove useful in any method which relies on affinity for HER2 of a reagent. Thus, the polypeptide may be used as a detection reagent, a capture reagent or a separation reagent in such methods, as a diagnostic agent for diagnostics in vivo or in vitro, or as a therapeutic agent in its own right or as a means for targeting other therapeutic or diagnostic agents to the HER2 protein. Methods that employ the polypeptide according to the invention in vitro may be performed in different formats, such as in microtiter plates, in protein arrays, on biosensor surfaces, on tissue sections, and so on.

Different modifications of, and/or additions to, the polypeptide according to the invention may be performed in order to tailor the polypeptide to the specific use intended, without departing from the scope of the present invention. Such modifications and additions are described in more detail below, and may comprise additional amino acids comprised in the same polypeptide chain, or labels and/or therapeutic agents that are chemically conjugated or otherwise bound to the polypeptide according to the invention.

Expressions like "binding affinity for HER2", "HER2 binding" and the like refer to a property of a polypeptide which may be tested e.g. by the use of surface plasmon resonance technology, such as in a Biacore® instrument (GE Healthcare). HER2 binding affinity may be tested in an experiment wherein HER2, or a fragment thereof, e.g. the extracellular domain, or a fusion protein thereof, is immobilized on a sensor chip of the instrument, and a sample containing the polypeptide to be tested is passed over the chip. Alternatively, the polypeptide to be tested is immobilized on a sensor chip of the instrument, and a sample containing HER2, or a fragment thereof, e.g. the extracellular domain, is passed over the chip. The skilled person may then interpret the sensorgrams obtained to establish at least a qualitative measure of the polypeptide's binding affinity for HER2. If a quantitative measure is sought, e.g. with the purpose to establish a certain $K_D$ value for the interaction, it is again possible to use surface plasmon resonance methods. Binding values may e.g. be defined in a Biacore® 2000 instrument (GE Healthcare). HER2, or a fragment thereof, e.g. the extracellular domain, is immobilized on a sensor chip of the instrument, and samples of the polypeptide whose affinity is to be determined are prepared by serial dilution and injected in random order. $K_D$ values may then be calculated from the results, using e.g. the 1:1 Langmuir binding model of the BIAevaluation 3.2 software provided by the instrument manufacturer.

The invention also encompasses polypeptides in which the HER2 binding polypeptide described above is present as a HER2 binding domain, to which additional amino acid residues have been added at either terminal. These additional amino acid residues may play a role in the binding of HER2 by the polypeptide, but may equally well serve other purposes, related for example to one or more of the production, purification, stabilization, coupling or detection of the polypeptide. Such additional amino acid residues may comprise one or more amino acid residues added for purposes of chemical coupling. An example of this is the addition of a cysteine residue at the very first or very last position in the polypeptide chain, i.e. at the N or C terminus. A cysteine residue to be used for chemical coupling may also be introduced by replacement of another amino acid on the surface of the protein domain, preferably on a portion of the surface that is not involved in target binding. Such additional amino acid residues may also comprise a "tag" for purification or detection of the polypeptide, such as a hexahistidyl ($His_6$) tag, or a "myc" tag or a "FLAG" tag for interaction with antibodies specific to the tag. The skilled person is aware of other alternatives.

In a specific embodiment of a polypeptide having additional amino acid residues, the invention provides an HER2 binding polypeptide comprising the amino acid sequence (SEQ ID NO: 5)
AEAKYAKEMR NAYWEIALLP NLTNQQKRAF IRKLYDDPSQ

SSELLSEAKK LNDSQAPKVD C.

In another specific embodiment of a polypeptide having additional amino acid residues, the invention provides an HER2 binding polypeptide comprising the amino acid sequence (SEQ ID NO: 6)
ESEKYAKEMR NAYWEIALLP NLTNQQKRAF IRKLYDDPSQ

SSELLSEAKK LNDSQAPK.

The "additional amino acid residues" discussed above may also constitute one or more polypeptide domain(s) with any desired function, such as the same binding function as the first, HER2-binding domain, or another binding function, or an enzymatic function, or a fluorescent function, or mixtures thereof.

Thus, the invention encompasses multimers of the polypeptide comprising any of the sequences SEQ ID NO: 1-6. It may be of interest, e.g. when using the polypeptide according to the invention for diagnosis or treatment of cancer or in a method of purification of HER2, to obtain even stronger binding of HER2 than is possible with one polypeptide according to the invention. In this case, the provision of a multimer, such as a dimer, trimer or tetramer, of the polypeptide may provide the necessary avidity effects. The multimer may consist of a suitable number of polypeptides according to the invention. The linked polypeptide "units" in a multimer according to the invention may be connected by covalent coupling using known organic chemistry methods, or expressed as one or more fusion polypeptides in a system for recombinant expression of polypeptides, or joined in any other fashion, either directly or via a linker, for example an amino acid linker.

Additionally, "heterogenic" fusion polypeptides, in which the polypeptide comprising any of the sequences SEQ ID NO: 1-6 constitutes a first domain, or first moiety, and the second and further moieties have other functions than binding HER2, are also contemplated and fall within the ambit of the present invention. The second and further moiety/moieties of the fusion polypeptide may comprise a binding domain with affinity for another target molecule than HER2. The result is then a fusion polypeptide having at least one HER2-binding domain and at least one domain with affinity for said other target molecule. This makes it possible to create multispecific reagents that may be used in several biotechnological applications, such as used as therapeutic agents or as capture, detection or separation reagents. The preparation of such multispecific multimers of polypeptides, in which at least one polypeptide domain comprises any of the sequences SEQ ID NO: 1-6, may be effected as described above for the multimer of several HER2 binding "units". The second or further moiety or moieties may be a variant of a domain derived from protein A of *Staphylococcus aureus*, such as a variant of the "Z domain" or "protein Z" (Nilsson B et al (1987), supra), or comprise an unrelated, naturally occurring or recombinant, protein (or a fragment thereof retaining the binding capability of the naturally occurring or recombinant protein) having a binding affinity for a target. An example of such a binding protein, which has an affinity for human serum albumin and may be used as fusion partner with the polypeptide according to the invention, is one of the albumin binding domains from protein G of *Streptococcus* strain G148 (Nygren P-Å et al (1988) Mol Recogn 1:69-74), such as the GA1, GA2 or GA3 domain. The GA3 domain of protein G is also denoted ABD, i.e. albumin binding domain. A fusion polypeptide between the HER2 binding polypeptide comprising any of the sequences SEQ ID NO: 1-6 and an albumin binding domain of streptococcal protein G thus falls within the scope of the present invention. When the polypeptide according to the invention is administered to a human subject as a diagnostic agent, therapeutic agent or as a targeting agent, the fusion thereof to a moiety which binds serum albumin may prove beneficial, in that the half-life in vivo of such a fusion protein is likely to be extended compared with the half-life of the HER2 binding moiety in isolation (this principle has been described e.g. in WO91/01743). Likewise, the fusion polypeptide is likely to exhibit a lower immunogenicity than the HER2 binding moiety in isolation, pursuant to the principles elucidated in WO2005/097202.

Other possibilities for the creation of fusion polypeptides are also contemplated. Thus, the polypeptide according to the first aspect of the invention may be covalently coupled to a second or further moiety or moieties, which in addition to, or instead of, target binding exhibit other functions. One example is a fusion between one or more polypeptide(s) comprising any one of the sequences with SEQ ID NO: 1-6 and an enzymatically active polypeptide serving as a reporter or effector moiety. Examples of reporter enzymes, which may be coupled to the polypeptide comprising any one of the sequences with SEQ ID NO: 1-6 to form a fusion protein, are known to the skilled person and include enzymes such as β-galactosidase, alkaline phosphatase, horseradish peroxidase, carboxypeptidase. Other options for the second and further moiety or moieties of a fusion polypeptide according to the invention include fluorescent polypeptides, such as green fluorescent protein, red fluorescent protein, luciferase and variants thereof.

Other options for the second and further moiety or moieties of a fusion polypeptide according to the invention include a moiety or moieties for therapeutic applications. In therapeutic applications, other molecules may also be coupled, covalently or non-covalently, to the inventive polypeptide by other means. Non-limiting examples include enzymes for ADEPT (antibody-directed enzyme prodrug therapy) applications using the polypeptide according to the invention for direction of the effector enzyme (e.g. carboxypeptidase); proteins for recruitment of effector cells and other components of the immune system; cytokines, such as IL-2, IL-12, TNFα, IP-10; procoagulant factors, such as tissue factor, von Willebrand factor; toxins, such as ricin A, *Pseudomonas* exotoxin, calcheamicin, maytansinoid; toxic small molecules, such as auristatin analogs, doxorubicin.

With regard to the description above of fusion proteins incorporating the HER2 binding polypeptide according to the invention, it is to be noted that the designation of first, second and further moieties is made for clarity reasons to distinguish between the HER2 binding moiety or moieties on the one hand, and moieties exhibiting other functions on the other hand. These designations are not intended to refer to the actual order of the different domains in the polypeptide chain of the fusion protein. Thus, for example, said first moiety may without restriction appear at the N-terminal end, in the middle, or at the C-terminal end of the fusion protein.

The invention encompasses polypeptides in which the HER2 binding polypeptide described above has been provided with a label group, such as at least one fluorophore, biotin or a radioactive isotope, for example for purposes of detection of the polypeptide. In particular the invention encompasses a radiolabeled polypeptide consisting of a radiochelate of a HER2 binding polypeptide as described above and a radionuclide, such as a radioactive metal.

A majority of radionuclides have a metallic nature and metals are typically incapable to form stable covalent bonds with elements presented in proteins and peptides. For this reason, labeling of targeting proteins with radioactive metals is performed with the use of chelators, multidentate ligands, which form non-covalent compounds, called chelates, with the metal. In an embodiment of the polypeptide according to the invention, the incorporation of a radionuclide is enabled through the provision of a chelating environment, through which the radionuclide may be coordinated, chelated or complexed to the polypeptide.

In a specific embodiment of the polypeptide of the invention, it comprises a tetradentate chelating environment characterized as an $N_3S$ chelator. As the term $N_3S$ indicates, the four attaching groups of such a chelator are formed from three nitrogen atoms and one sulfur atom. In an $N_3S$ chelator, the N and S atoms are spatially arranged to provide a suitable "pocket" for complexing or attachment of the radioactive metal.

An $N_3S$ chelator may be provided through a suitable choice of amino acid residues in the amino acid sequence of the polypeptide.

For example, an $N_3S$ chelating environment may be provided through the coupling of mercaptoacetyl to the N-terminus of the polypeptide according to the invention. In this embodiment, the mercaptoacetyl provides the necessary S atom, whereas the first three N atoms in the peptide backbone constitute the three N atoms of the tetradentate chelator. Preferably, mercaptoacetyl is coupled to a polypeptide comprising the amino acid sequence SEQ ID NO:4 as the most N-terminal amino acid sequence, resulting in a polypeptide comprising the amino acid sequence maESEKYAKEX$_1$R NAYWEIALLP NLTNQQKRAF IRKLYDDPSQ SSELLX$_2$EAKK LNDSQ,
wherein ma is mercaptoacetyl, $X_1$ in position 9 is M, I or L, and $X_2$ in position 46 is S or C. In a particularly preferred embodiment of this the polypeptide has the sequence:

```
                                    (SEQ ID NO: 7)
maESEKYAKEMR NAYWEIALLP NLTNQQKRAF IRKLYDDPSQ

SSELLSEAKK LNDSQAPK,.
wherein ma is mercaptoacetyl
```

In an alternative embodiment, the three N groups may be provided by the N atoms of three consecutive peptide bonds in the polypeptide chain, of which the last is a cysteine residue, which comprises an SH group on its side-chain. The S atom of the cysteine side-chain constitutes the S atom in the $N_3S$ chelator. Alternatively speaking, the $N_3S$ chelator is provided in the form of a tripeptide sequence XXC, wherein X is any amino acid residue. Such a tripeptide sequence may be comprised in the polypeptide according to the invention either initially or added as one or more additional amino acids. It is preferred that the cysteine residue is the one situated at the C-terminal end of SEQ ID NO:5 or that an additional cysteine is situated immediately at the C-terminal of any of SEQ ID NO:1-4 or 6-7. The cysteine residue may also be followed by one or more other amino acid residue(s).

A polypeptide according to the invention which comprises a tetradentate chelating environment characterized as an $N_3S$ chelator, provided either by mercaptoacetyl coupled to the N-terminal and the nitrogen atoms of three consecutive peptide bonds, or by the nitrogen atoms of three consecutive peptide bonds and a cysteine residue at the C-terminal of the polypeptide, may be used to provide a radiolabeled polypeptide consisting of a radiochelate of the HER2 binding polypeptide and a radionuclide suitable for medical imaging, said radionuclide being $^{99m}$Tc (Engfeldt et al (2007) Eur. J. Nucl. Med. Mol. Imaging. 34(5):722-22; Engfeldt et al (2007) Eur. J. Nucl. Med. Mol. Imaging. 34(11):1843-53), or with a radionuclide suitable for therapy, said radionuclide being selected from the group consisting of $^{186}$Re and $^{188}$Re. In some embodiments, the radionuclide is complexed with the HER2 binding polypeptide via the chelating environment.

When the polypeptide according to the invention comprises two, three or more XXC tripeptides, it is preferably the terminal one that is used to complex the radionuclide. When the polypeptide is radiolabeled in this way, the other XXC tripeptide(s) is/are preferably protected.

One particularly preferred embodiment of a radiolabeled polypeptide according to the invention is a radiochelate of a HER2 binding polypeptide having the amino acid sequence maESEKYAKEMR NAYWEIALLP NLTNQQKRAF IRKLYDDPSQ SSELLSEAKK LNDSQAPK, wherein ma is mercaptoacetyl (SEQ ID NO:7) and $^{99m}$Tc.

The hypothetical structures of $^{99m}$Tc chelated using maESE- at the N-terminal or -VDC at the C-terminal of the polypeptide are:

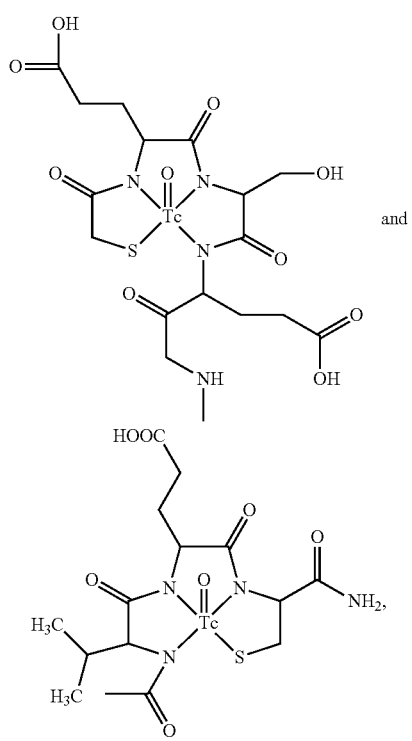

respectively.

In an alternative embodiment of a polypeptide according to the invention, a polyaminopolycarboxylate chelator is used to incorporate the radionuclide. Preferably the polypeptide then comprises at least one cysteine, and most preferably it comprises only one cysteine. The cysteine(s) may be present in the polypeptide according to the invention either initially or added at a later stage as one or more additional amino acids.

A skilled person could also foresee a number of other chelators, capable to chelate such cores as "naked" Me, Me=O, O=Me=O, Me≡N, Me(CO)$_3$, or HYNIC-Me-co-ligand(s) core (wherein Me is a radioactive isotops of Tc or Re), which can be attached to a polypeptide site-specifically during peptide synthesis or conjugated to a recombinantly produced polypeptide using known conjugation chemistry for radiolabeling. Preferably, such chelators have a hydrophilic character. A good overview of such chelators is provided in Liu S and Edwards D S (1999) Chem. Rev. 99(9): 2235-68.

One can distinguish two classes of polyaminopolycarboxylate chelators: macrocyclic and acyclic.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid) (see below). Several different DOTA-based compounds suitable for use as chelators with the polypeptides according to the invention are commercially available, for example from Macrocyclics Inc., USA, and examples are shown below.

In this schematic, A is DOTA, B is amino-reactive 4-isothiocyanato-benzyl-DOTA, C is DOTA-TFP ester, and D is thiol-reactive maleimido-mono-amide DOTA.

The high kinetic inertness, i.e. the slow rate of dissociation of metal from DOTA, favors stable attachment of a radionuclide. However, elevated temperatures are required for labeling due to a slow association rate. For this reason, DOTA derivatives are widely used for labeling of short peptides, which are relatively insensitive to heating to 60-90° C.

One preferred derivative for use as chelator in the present invention is 1,4,7,10-tetraazacyclododecane-1,4,7-tris-acetic acid-10-maleimidoethylacetamide.

As disclosed above, the polypeptide according to the invention may for example comprise the amino acid sequence SEQ ID NO:5. In a more specific embodiment, the polypeptide comprises SEQ ID NO:5 and has a tetraazacyclo compound coupled to amino acid residue C61. In a particularly preferred embodiment, the tetraazacyclo compound is 1,4,7,10-tetraazacyclododecane-1,4,7-tris-acetic acid-10-maleimidoethylacetamide, which has been coupled to the polypeptide through reaction of the SH group of residue C61 with the maleimido moiety of the tetraazacyclo compound. One particularly preferred embodiment of the invention is thus a HER2 binding polypeptide comprising the amino acid sequence AEAKYAKEMR NAYWEIALLP NLTNQQKRAF IRKLYDDPSQ SSELLSEAKK LNDSQAPKVD C (SEQ ID NO:5) coupled to 1,4,7,10-tetraazacyclododecane-1,4,7-tris-acetic acid-10-maleimidoethylacetamide.

The most commonly used acyclic polyaminopolycarboxylate chelators are different derivatives of DTPA (diethylenetriamine-pentaacetic acid), such as those shown in the schematic below, where A is DTPA, B is the amino-reactive derivative isothiocyanatobenzyl-DTPA, C is the amino-reactive derivative semirigid 2-(para-isothiocyanatobenzyl)-6-methyl-DTPS (IB4M), and D is the amino-reactive derivative CHX-A"-DTPA.

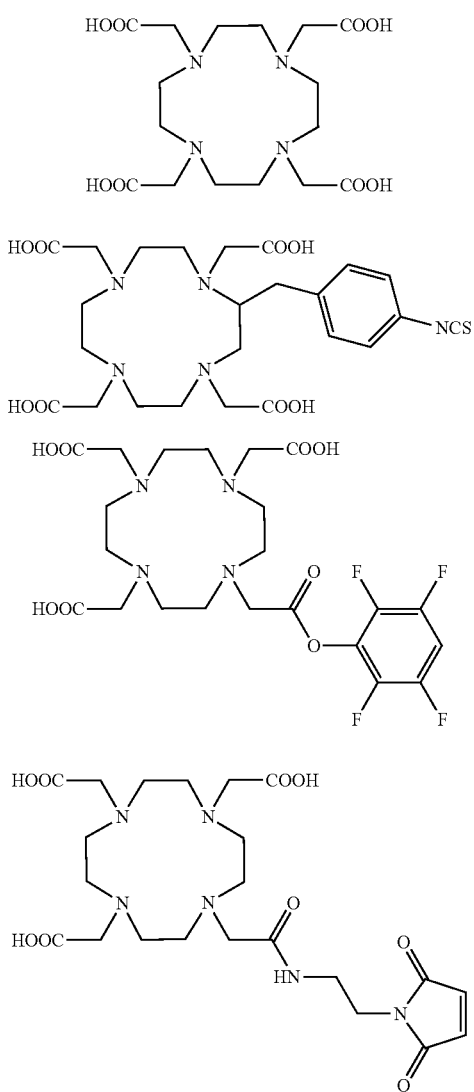

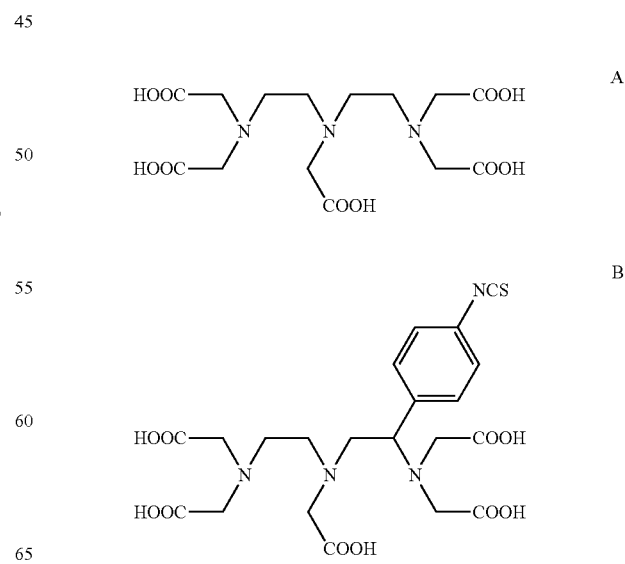

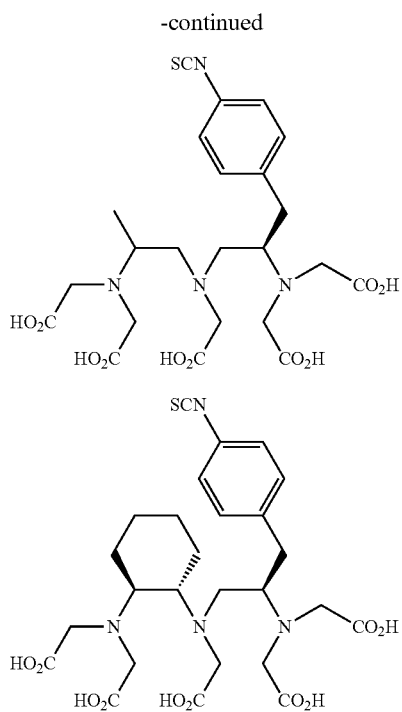

It has been found that backbone-modified semi-rigid variants of DTPA provide adequate stability for labeling with $^{90}$Y of e.g. Zevalin®. Though acyclic chelators are less inert, and consequently, less stable than macrocyclic ones, their labeling is rapid enough even at ambient temperature. For this reason, they might be preferred for labeling of monoclonal antibodies, which cannot tolerate heating. Detailed protocols for coupling of polyaminopolycarboxylate chelators to targeting proteins and peptides have been published by Cooper and co-workers (Nat. Protoc. 1: 314-7. 2006) and Sosabowski and Mather (Nat. Protoc. 1: 972-6, 2006).

A polypeptide according to the invention coupled to a polyaminopolycarboxylate chelator may be used to provide a radiolabeled polypeptide consisting of a radiochelate of the HER2 binding polypeptide coupled to the chelator and a radionuclide suitable for medical imaging, said radionuclide being selected from the group consisting of $^{61}$Cu, $^{64}$Cu, $^{66}$Ga, $^{67}$Ga, $^{68}$Ga, $^{110m}$In, $^{111}$In, $^{44}$Sc and $^{86}$Y, or with a radionuclide suitable for therapy, said radionuclide being selected from the group consisting of $^{225}$Ac, $^{212}$Bi, $^{213}$Bi, $^{67}$Cu, $^{166}$Ho, $^{177}$Lu, $^{212}$Pb, $^{149}$Pm, $^{153}$Sm, $^{227}$Th and $^{90}$Y, wherein the radionuclide is complexed with the HER2 binding polypeptide via the chelating environment.

One particularly preferred embodiment of a radiolabeled polypeptide according to the invention is radiochelate of a HER2 binding polypeptide having the amino acid sequence AEAKYAKEMR NAYWEIALLP NLTNQQKRAF IRKLY-DDPSQ SSELLSEAKK LNDSQAPKVD C (SEQ ID NO:5) coupled to 1,4,7,10-tetraazacyclododecane-1,4,7-tris-acetic acid-10-maleimidoethylacetamide and $^{111}$In.

One particularly preferred embodiment of a radiolabeled polypeptide according to the invention is radiochelate of a HER2 binding polypeptide having the amino acid sequence AEAKYAKEMR NAYWEIALLP NLTNQQKRAF IRKLY-DDPSQ SSELLSEAKK LNDSQAPKVD C (SEQ ID NO:5) coupled to 1,4,7,10-tetraazacyclododecane-1,4,7-tris-acetic acid-10-maleimidoethylacetamide and $^{61}$Cu or $^{64}$Cu.

One particularly preferred embodiment of a radiolabeled polypeptide according to the invention is radiochelate of a HER2 binding polypeptide having the amino acid sequence AEAKYAKEMR NAYWEIALLP NLTNQQKRAF IRKLY-DDPSQ SSELLSEAKK LNDSQAPKVD C (SEQ ID NO:5) coupled to 1,4,7,10-tetraazacyclododecane-1,4,7-tris-acetic acid-10-maleimidoethylacetamide and $^{66}$Ga, $^{67}$Ga or $^{68}$Ga.

One particularly preferred embodiment of a radiolabeled polypeptide according to the invention is radiochelate of a HER2 binding polypeptide having the amino acid sequence AEAKYAKEMR NAYWEIALLP NLTNQQKRAF IRKLY-DDPSQ SSELLSEAKK LNDSQAPKVD C (SEQ ID NO:5) coupled to 1,4,7,10-tetraazacyclododecane-1,4,7-tris-acetic acid-10-maleimidoethylacetamide and $^{86}$Y.

The radiolabeled polypeptide according to the invention may also be obtained by indirect labeling of a HER2 binding polypeptide as described above. Preferably the polypeptide comprises at least one cysteine, and most preferably it comprises only one cysteine. The cysteine(s) may be present in the polypeptide according to the invention either initially or added at a later stage as one or more additional amino acids. For indirect labeling with for example $^{18}$F, $^{76}$Br, different iodine isotopes and $^{211}$At, intermediate "linker molecules" are used for labeling. Such a linker should contain two functional moieties, one providing rapid and efficient radiolabeling, and another enabling rapid and efficient coupling to the proteins, e.g. to amine groups, or preferably to the thiol group of a unique cysteine. For example a malemide group reacts with thiol groups to form a stable thioether bond. The idea is to first react the "linker molecule" with the radiolabel and subsequently with the thiol group of the protein.

Several alternatives are thoroughly investigated for radioiodination, where radiolabeling of the linker molecule has been done e.g. on an activated phenolic ring or an aromatic ring with a suitable leaving group. A detailed protocol for preparation of non-labeled linker and indirect radioiodination using N-succinimidyl 3-[*I]iodobenzoate has been provided by Vaidyanathan et al. (Vaidyanathan G and Zalutsky M R (2006) Nat. Protoc. 1(2):707-13). An example of indirect radioiodination using N-succinimidyl trimethylstannyl-benzoate is illustrated in the schematic below.

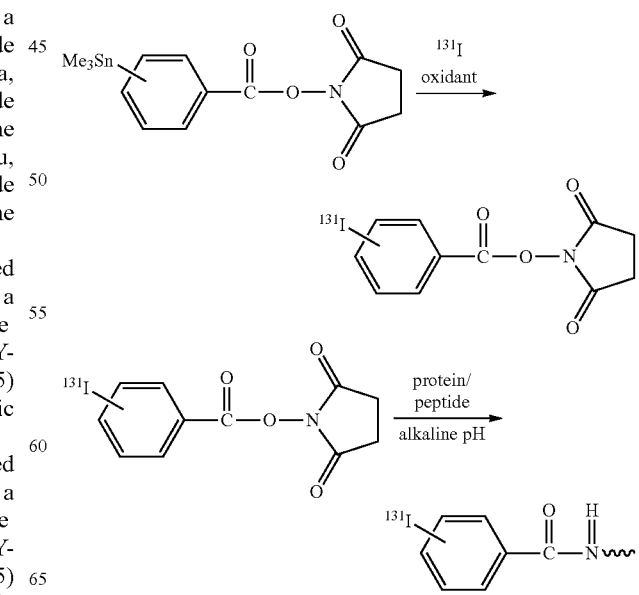

In this schematic, the linker molecule is first radioiodinated in acidic conditions and then coupled to free amine (N-terminal of the ε-amino group of lysine) in alkaline conditions. Both meta- and para-iododerivatives of benzoate have been described in the literature.

The linker molecule may comprise an aryl group linking the radiolabel (e.g. at the 2-, 3- or 4-position), provided that when the radiolabel is $^{76}$Br, then the linker molecule does not include a phenolic OH-group. Non-limiting examples of linker molecules comprises a heterocyclic imide that can be used to link the inventive polypeptide and radiolabel include N-[2-benzamidoethyl]malemide, 4-maleimidobenzophenone (BPMaI), succinimidyl 4-(p-maleimidophenyl)butyrate (SMPB), 4-(4-N-maleimidophenyl)butyric acid hydrazide hydrochloride (MPBH), and maleimidobenzoyl-N-hydroxysuccinimide ester (MBS).

N-[2-benzamidoethyl]malemide may be reacted with $^{18}$F to form N-[2-(4-($^{18}$F-fluorobenzamido)ethyl]malemide. Likewise it may be reacted with $^{76}$Br as described by Cai et al. (J. Nucl. Med. 47:1172-80, 2006).

The present invention also concerns different aspects of using the above-described HER2 binding polypeptide, as well as various methods for treatment, diagnosis and detection in which the polypeptide is useful due to its binding characteristics. When referring to the "HER2 binding polypeptide" in the following description of these uses and methods, this term is intended to encompass the HER2 binding polypeptide alone, but also all those molecules based on this polypeptide described above that e.g. incorporate the HER2 binding polypeptide as a moiety in a fusion protein and/or are conjugated to a label, a chelator, a therapeutic and/or diagnostic agent and/or are provided with additional amino acid residues as a tag or for other purposes. As explained above, such fusion proteins, derivatives etc form a part of the present invention.

Thus, in one such aspect, the invention provides a method for in vivo imaging of the body of a mammalian, including human, subject having or suspected of having a cancer characterized by overexpression of HER2, the method comprising the steps:

administration of a radiolabeled polypeptide as described above, comprising a radionuclide suitable for medical imaging, into the body of a mammalian subject; and obtaining an image of at least a part of the subject's body using a medical imaging instrument, said image indicating the presence of the radionuclide inside said body. Preferably the image is obtained within 1-72 hours, or in some cases even more preferably within 1-24 hours, of administration of the radiolabeled polypeptide to the body. The time between the administration and the obtaining of the image is dependent on the half-life of the radionuclide used. It is possible to repeat the step of obtaining an image two, three or more times, whereby a series of images is obtained. This is useful when one seeks to follow the biodistribution over time of a targeting agent, and allows for pharmacokinetic studies. The skilled person appreciates that any number of images could be obtained, in order to achieve the requisite degree of time resolution in such a study.

In one embodiment of the imaging method according to the invention, the method comprises, before the administration step, a preparatory step of preparing a radiolabeled polypeptide according to the invention, which step comprises mixing of a polypeptide according to the first aspect with a radionuclide suitable for medical imaging.

In a more specific embodiment of the imaging method according to the invention, the method comprises, before the administration step, a preparatory step of preparing a radiolabeled polypeptide of i) a polypeptide whose amino acid sequence consists of SEQ ID NO:7 with ii)$^{99m}$Tc, which step comprises mixing the polypeptide with $^{99m}$Tc-pertechnetate in the presence of appropriate reducing agent, e.g. stannous chloride or fluoride, in an appropriate buffer. This might be performed also in the presence of an intermediate weak chelator, e.g. tartrate, or citrate or gluconate.

In another specific embodiment of the imaging method according to the invention, the method comprises, before the administration step, a preparatory step of preparing a radiolabeled polypeptide of i) a polypeptide whose amino acid sequence consists of SEQ ID NO:5 conjugated to 1,4,7,10-tetraazacyclododecane-1,4,7-tris-acetic acid-10-maleimido-ethylacetamide with ii) $^{111}$In, which step comprises mixing the conjugate with $^{111}$In in an appropriate buffer preventing formation of non-soluble colloids, for example (but not limited to) acetate or citrate buffer.

In another specific embodiment of the imaging method according to the invention, the method comprises, before the administration step, a preparatory step of preparing a radiolabeled polypeptide of i) a polypeptide whose amino acid sequence consists of SEQ ID NO:5 conjugated to 1,4,7,10-tetraazacyclododecane-1,4,7-tris-acetic acid-10-maleimido-ethylacetamide with ii) $^{61}$Cu or $^{64}$Cu, which step comprises mixing the conjugate with $^{61}$Cu or $^{64}$Cu in an appropriate buffer preventing formation of non-soluble colloids, for example (but not limiting to) acetate or citrate buffer.

In another specific embodiment of the imaging method according to the invention, the method comprises, before the administration step, a preparatory step of preparing a radiolabeled polypeptide of i) a polypeptide whose amino acid sequence consists of SEQ ID NO:5 conjugated to 1,4,7,10-tetraazacyclododecane-1,4,7-tris-acetic acid-10-maleimido-ethylacetamide with ii) $^{66}$Ga, $^{67}$Ga or $^{68}$Ga, which step comprises mixing the conjugate with $^{66}$Ga, $^{67}$Ga or $^{68}$Ga in an appropriate buffer preventing formation of non-soluble colloids, for example (but not limited to) acetate or citrate buffer.

In some embodiments of this aspect of the invention, said cancer is selected from breast cancer, ovarian cancer, stomach cancer, bladder cancer, salivary cancer, lung cancer and cancer in the esophagus.

In another aspect, the invention provides a radiolabeled polypeptide as described above for use in diagnosis. The term "diagnosis" is used herein in order to describe the act or process of identifying or determining the nature and cause of a disease through evaluation of patient history, examination and review of laboratory data.

The radiolabeled polypeptide may be used in diagnosis of a cancer belonging to the group of cancers characterized by frequently occurring overexpression of HER2. The term "frequently occurring" is used herein to denote that overexpression of HER2 is present in at least 10% of all patients having a specific cancer. The radiolabeled polypeptide may thus be used in the process of deciding whether or not a patient has such a cancer or not. It may also be used in the process of deciding on suitable treatment of a patient. Particularly, detection of HER2 overexpression may be useful for stratification of patients for HER2 targeted therapy, e.g. treatment with trastuzumab (Herceptin®).

The radiolabeled polypeptide may also be used in diagnosis and/or molecular characterization of a cancer selected from breast cancer, ovarian cancer, stomach cancer, bladder cancer, salivary cancer, lung cancer and cancer in the esophagus. In this context molecular characterization relates to the characterization of HER2 expression, i.e. for example to determine whether or not there is any expression of HER2, to determine the amount of HER2 expression, e.g. before and after treatment which can be accomplished by obtaining images before and after treatment, and to determine the extent or anatomical content of HER2 expression, e.g. for surgical purposes.

Also provided, in yet another aspect of the invention, is the use of a radiolabeled polypeptide as described above in the preparation of a diagnostic agent for imaging in vivo of the body of a mammalian, including human, subject.

In another application aspect, the invention provides a method of treatment of a mammalian, including human, subject having a cancer characterized by overexpression of HER2, comprising the step of administering a radiolabeled polypeptide as described above, comprising a radionuclide suitable for therapy, into the body of said mammalian subject in a therapeutically effective amount.

In one embodiment of this aspect, the method comprises, before the administration step, a preparatory step of preparing a radiolabeled polypeptide according to the invention, which step may comprise:

mixing of a polypeptide according to the first aspect with a metal radionuclide suitable for therapy in an appropriate buffer; or mixing of a polypeptide according to the first aspect with perrhenate in appropriate buffer in the presence of appropriate reducing agent; this might be performed also in the presence of an intermediate weak chelator, e.g. tartrate, or citrate or gluconate; or mixing of a polypeptide according to the first aspect with a reactive intermediate of rhenium, such as a tricarbonyl complex; or mixing of a polypeptide according to the first aspect with a reactive intermediate with attached halogen atom in an appropriate buffer. This mixing may be performed in the presence of substances designated to suppress radiolysis of polypeptide, such as ascorbic acid or gentisic acid.

In some embodiments of this aspect of the invention, said cancer is selected from breast cancer, ovarian cancer, stomach cancer, bladder cancer, salivary cancer, lung cancer and cancer in the esophagus.

In another aspect, the invention provides a radiolabeled polypeptide as described above for use in therapy, such as for use in therapy of a cancer characterized by overexpression of HER2, for example for use in therapy of a cancer selected from breast cancer, ovarian cancer, stomach cancer, bladder cancer, salivary cancer, lung cancer and cancer in the esophagus.

Also provided, in yet another aspect of the invention, is use of a radiolabeled polypeptide as described above in the preparation of a medicament for treatment of a cancer characterized by overexpression of HER2, such as a cancer selected from breast cancer, ovarian cancer, stomach cancer, bladder cancer, salivary cancer, lung cancer and cancer in the esophagus.

Another aspect of the present invention relates to a nucleic acid molecule comprising a sequence which encodes a polypeptide as described above.

A further aspect of the present invention relates to an expression vector comprising the nucleic acid molecule of the previous aspect, and other nucleic acid elements that enable production of the polypeptide according to the invention through expression of the nucleic acid molecule.

Yet another aspect of the present invention relates to a host cell comprising the expression vector of the previous aspect.

The latter three aspects of the invention are tools for the production of a polypeptide according to the invention, and the skilled person will be able to obtain them and put them into practical use without undue burden, given the information herein concerning the polypeptide that is to be expressed and given the current level of skill in the art of recombinant expression of proteins.

However, the polypeptide according to the invention may also be produced by other known means, including chemical synthesis or expression in different prokaryotic or eukaryotic hosts, including plants and transgenic animals.

The invention will now be illustrated in detail through the description of experiments conducted in accordance therewith. The examples to follow are not to be interpreted as limiting. In the examples, reference is made to the appended figures.

BRIEF DESCRIPTION OF THE FIGURES

The sequences of the Affibody® molecules are given in Table 1 below.

EXAMPLES

Example 1

Figure 1:
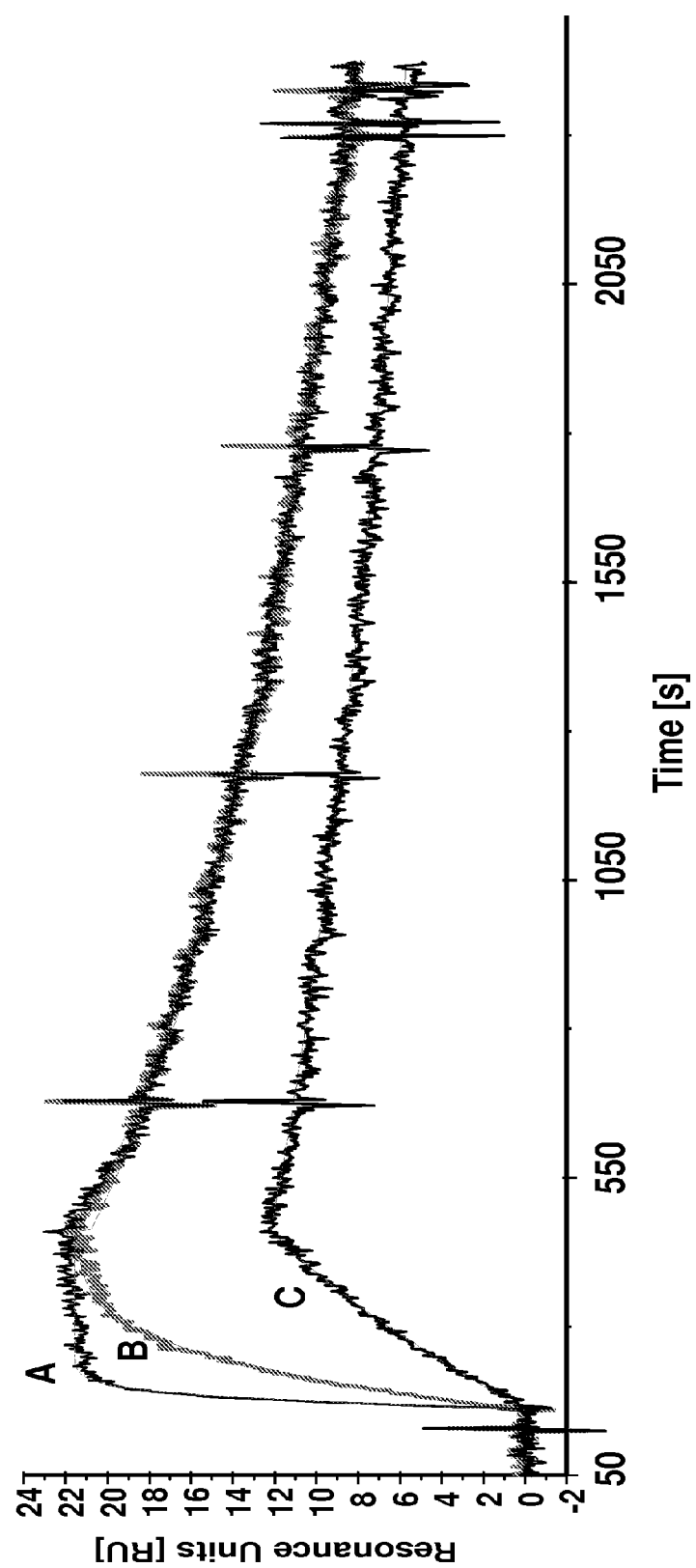
FIG. 1 shows Biacore sensorgrams obtained after injection of A: 7.8 nM; B: 1.9 nM and C, 0.49 nM of Affibody® molecule II over a sensor chip having HER2/Fc chimeric fusion protein immobilized thereto. The SH-group of the C-terminal cysteine was blocked with N-ethylmaleimide (NEM).

Preparation of a Polypeptide According to the Invention

Summary

In this example, selected HER2 specific Affibody® molecules are sub-cloned into a pET System expression vector, expressed in a larger scale in appropriate bacterial cells and purified according to the protocols below. The amino acid sequences of the corresponding full length HER2 specific Affibody® molecules are listed in Table 1 as Affibody® molecules I-XI.

Cloning of Affibody® Molecules

The genes encoding Affibody® molecules I-VIII were PCR-amplified by using two oligonucleotides (jointly encompassing the Affibody® sequence) as template. For each construct a specific pair of template oligonucleotides (each 102 b long) with a complementary overlap of 28 bp was used. The Affibody® gene was amplified with a forward primer (sense), including an NdeI site and an ATG start codon (for Affibody® molecule I a His$_6$-tag encoding sequence was also included in the primer) and a reverse primer (anti-sense) with codons for the C-terminal amino acids, stop codon and a NotI site.

The Affibody®-Albumin Binding Domain (ABD) gene fusion in Affibody® molecule IX was produced by overlap extension PCR. The Affibody® molecule encoding fragment was generated as described above for Affibody® molecules I-VIII, with the exception that the reverse primer included a linker sequence (with a Cys codon) and the 5'-end of the ABD gene. The ABD gene was amplified with a forward primer, including the 3'-end of the Affibody® gene and linker sequence and a reverse primer with stop codon and a NotI site. Subsequently, the two PCR-products with 25 bp overlap were used as template in the final PCR-amplification using Affibody® gene forward primer and ABD gene reverse primer, generating the Affibody®-ABD gene fusion.

The PCR-products were digested with the restriction enzymes NdeI and NotI and ligated in a T7-expression vector previously digested with the same enzymes.

TABLE 1

Amino acid sequence of produced Affibody ® molecules.

| Affibody ® molecule | Amino acid sequence of the mature protein |
|---|---|
| I | GSSHHHHHHL QVDAKYAKEM RNAYWEIALL PNLTNQQKRA FIRKLYDDPS QSSELLSEAK KLNDSQAPK |
| II (SEQ ID NO: 5) | AEAKYAKEMR NAYWEIALLP NLTNQQKRAF IRKLYDDPSQ SSELLSEAKK LNDSQAPKVD C |
| III | AEAKYAKEMR NAYWEIALLP NLTNQQKRAF IRKLYDDPSQ SSELLSEAKK LNDSQAPKC |
| IV | AEAKYAKEIR NAYWEIALLP NLTNQQKRAF IRKLYDDPSQ SSELLSEAKK LNDSQAPKC |
| V | AEAKYAKELR NAYWEIALLP NLTNQQKRAF IRKLYDDPSQ SSELLSEAKK LNDSQAPKC |
| VI | AEAKYAKEMR NAYWEIALLP NLTNQQKRAF IRKLYDDPSQ SSELLCEAKK LNDSQAPK |
| VII | AEAKYAKEIR NAYWEIALLP NLTNQQKRAF IRKLYDDPSQ SSELLCEAKK LNDSQAPK |
| VIII | AEAKYAKELR NAYWEIALLP NLTNQQKRAF IRKLYDDPSQ SSELLCEAKK LNDSQAPK |
| IX | AEAKYAKEMR NAYWEIALLP NLTNQQKRAF IRKLYDDPSQ SSELLSEAKK LNDSQAPG-CGS-"ABD" |

TABLE 1 -continued

Amino acid sequence of produced Affibody ® molecules.

| Affibody ® molecule | Amino acid sequence of the mature protein |
|---|---|
| X (SEQ ID NO: 7) | maESEKYAKEMR NAYWEIALLP NLTNQQKRAF IRKLYDDPSQ SSELLSEAKK LNDSQAPK |
| XI | YAKELRNAYW EIALLPNLTN QQKRAFIRKL YDDPSQSSEL LCEAKKLNDS QA |

Expression and Harvesting of Affibody® Molecules

The resulting expression plasmids were transformed to *Escherichia coli* BL21(DE3) cells using electroporation. Bacteria containing expression plasmids were picked from selective agar containing Kanamycin and grown at 37° C. in 800 ml of TSB+YE-medium (30 g/l Tryptic Soy Broth+5 g/l Yeast Extract) supplemented with 50 mg/l Kanamycin using a multifermentor system (System Greta, Belach Bioteknik AB, Sweden). At an optical density ($OD_{600nm}$) of ~1 the expression of Affibody® molecules was automatically induced through the addition of 0.5 mM of IPTG. Five hours after the addition of inducing agent, the cultures were automatically cooled down to <12° C. The cultures were then harvested through centrifugation (20 min at 15,900×g) and 5-10 g of bacterial cell pellet were harvested and stored in a freezer (−20° C.).

Purification of Affibody® Molecule I

The cell pellet (3 g) was resuspended in 30 ml of a pH 8 buffer containing 7 M urea and 1000 units Benzonase (Merck). After 30 minutes incubation, the lysate was clarified by centrifugation and the supernatant containing the $His_6$-tagged Affibody® molecule was applied on a 1.5 ml Superflow Ni-NTA column (Qiagen). The column was washed with 20 ml of a pH 6.3 buffer containing 7 M urea and eluted with a pH 4.5 buffer containing 8 M urea. Finally, the buffer was exchanged to 1×PBS (2.68 mM KCl, 137 mM NaCl, 1.47 mM $KH_2PO_4$, 8.1 mM $Na_2HPO_4$, pH 7.4) by using a PD-10 column (GE Healthcare).

Purification of Affibody® Molecules II-VIII

The cell pellet (10 g) was resuspended in 100 ml 20 mM Tris-HCl pH 7.5, supplemented with 2000 units Benzonase (Merck), disrupted by sonication and heated to 75° C. for 10 minutes. The heat treated lysate was clarified by centrifugation and applied on a XK26 column packed with 25 ml Q-Sepharose FF (GE Healtcare), previously equilibrated with 20 mM Tris-HCl pH 7.5. The flow through fraction from the column was collected and Affibody® molecules with a C-terminal cysteine were incubated with 20 mM DTT for 1 hour at room temperature. ACN was added to 5% and applied on a 3 ml Resource 15RPC column (GE Healtcare), previously equilibrated with 5 ACN, 0.1% TFA in water. After washing of the column with 5 column volumes (CV) 5% ACN, 0.1% TFA in water, bound proteins were eluted with a linear gradient 5-32% ACN, 0.1% TFA in water during 20 CV. Fractions containing Affibody® molecules were identified by SDS-PAGE analysis and pooled. Finally, the buffer was exchanged to 1×PBS by using a HiPrep 26/10 Desalting column (GE Healthcare).

Purification of Affibody® Molecule IX

The cell pellet (5 g) was resuspended in 50 ml TST-buffer (25 mM Tris-HCl, 200 mM NaCl, 1 mM EDTA, 0.05% Tween 20, pH 8.0) and disrupted by sonication. After clarification by centrifugation, the supernatant was applied on a XK26 column (GE Healtcare) packed with 20 ml HSA-Sepharose (human serum albumin immobilized on CNBr-activated Sepharose 4 Fast Flow, GE Healtcare). The column was washed with 10 CV TST-buffer followed by 5 CV 5 mM $NH_4Ac$ pH 5.6. Bound ABD-tagged Affibody® molecule was eluted with 0.5 M HAc pH 2.8. Finally, the buffer was exchanged to 1×PBS by using a HiPrep 26/10 Desalting column (GE Healthcare).

Example 2

HER2 Binding Properties of a Polypeptide According to the Invention In Vitro

Summary

In the experiments making up this example the binding of polypeptides according to the invention were analyzed using Surface Plasmon Resonance (SPR) in a Biacore® 2000 system. The HER2 target binding activity is shown for the Affibody® molecules II (SEQ ID NO:5), II with DOTA coupled to the C-terminal cysteine and X (SEQ ID NO:7).

Biosensor Analysis

The recombinant human HER2/Fc (ErbB2/Fc) chimeric protein, consisting of the extracellular domain of ErbB2 (HER2, $Met^1$-$Thr^{652}$) fused to the Fc region of human $IgG_1$ ($Pro^{100}$-$Lys^{330}$) with a C-terminal $His_5$-tag (R&D Systems #1129-ER), was immobilized (1800 resonance units (RU)) onto a surface of a CM5 sensor chip using amine coupling chemistry. One surface on the chip was activated and deactivated for use as reference cell. Affibody® molecules diluted in HBS-EP buffer (10 mM HEPES, 150 mM NaCl, 3 mM EDTA, 0.005% surfactant P-20, pH 7.4) were used as analytes.

For analysis of the binding kinetics, three analyte concentrations were injected in duplicates over the chip using a constant flow-rate of 50 µl/minute. The association phase was 5 minutes followed by a long dissociation phase (30 min) to account for the slow off rate of the Affibody® molecules. The dissociation equilibrium constant ($K_D$), the association rate constant ($k_a$) and the dissociation rate constant ($k_d$) were calculated using the 1:1 Langmuir binding model with mass transfer correction of the BIAevaluation 4.1 software (GE Healthcare).

Blocking of the SH-group of Cysteine

Affibody® molecules with a single C-terminal cysteine were treated with N-ethylmaleimide (NEM, Pierce No. 23030) to block the SH-group of cysteine and thereby prevent dimerization of the molecules. The Affibody® molecule II (SEQ ID NO:5) was reduced by treating 1 ml (2.1 mg) of the peptide with 10 µl Tris-HCl pH 8.5 and 40 µl 0.5 M dithiothreitol (DTT) for two hours at room temperature. Excess of DDT was removed by gel filtration on NAP5-columns (GE Healthcare) equilibrated with coupling buffer (100 mM sodium phosphate, 150 mM NaCl, pH 7.0): load column with 0.5 ml reduced protein, elute protein with 1 ml coupling buffer.

Blocking of the free SH-group was done using a 20 fold molar excess of NEM to protein: add 15 µl NEM solution in water (200 mM) to 0.5 ml of reduced protein solution (1 mg/ml) and incubate for one hour at room temperature on a head-over-head mixer. Excess NEM was removed by gel filtration on NAP5-columns as described above, however with PBS as equilibration buffer.

Coupling of Maleimide-DOTA to the C-Terminal Cysteine 3 mg of Affibody® molecule II (SEQ ID NO:5) was reduced with 20 mM DTT at 40° C. for 30 minutes. Excess DTT was removed by buffer exchange on a PD-10 column to 0.2M NH$_4$Acetate pH 5.5. The coupling was performed with a three-fold molar excess of chelator, maleimido-mono-amide-DOTA (Mal-DOTA, Macrocyclics No.B-272) solution in water (1 mg/ml). The mixture was incubated for 1 hour at 40° C. with continuous shaking. Purification from non-conjugated chelators was made on a semi-preparative RPC column, Zorbax 300SB C18, 9.4×250 mm, 5 µm. The coupling degree of the purified material was analyzed by HPLC-MS on a Zorbax 300SB C8 150×2.1 mm, 3.5 µm analytical column. Only maleimide-DOTA conjugated Affibody® molecules was detected by the method.

Figure 2:
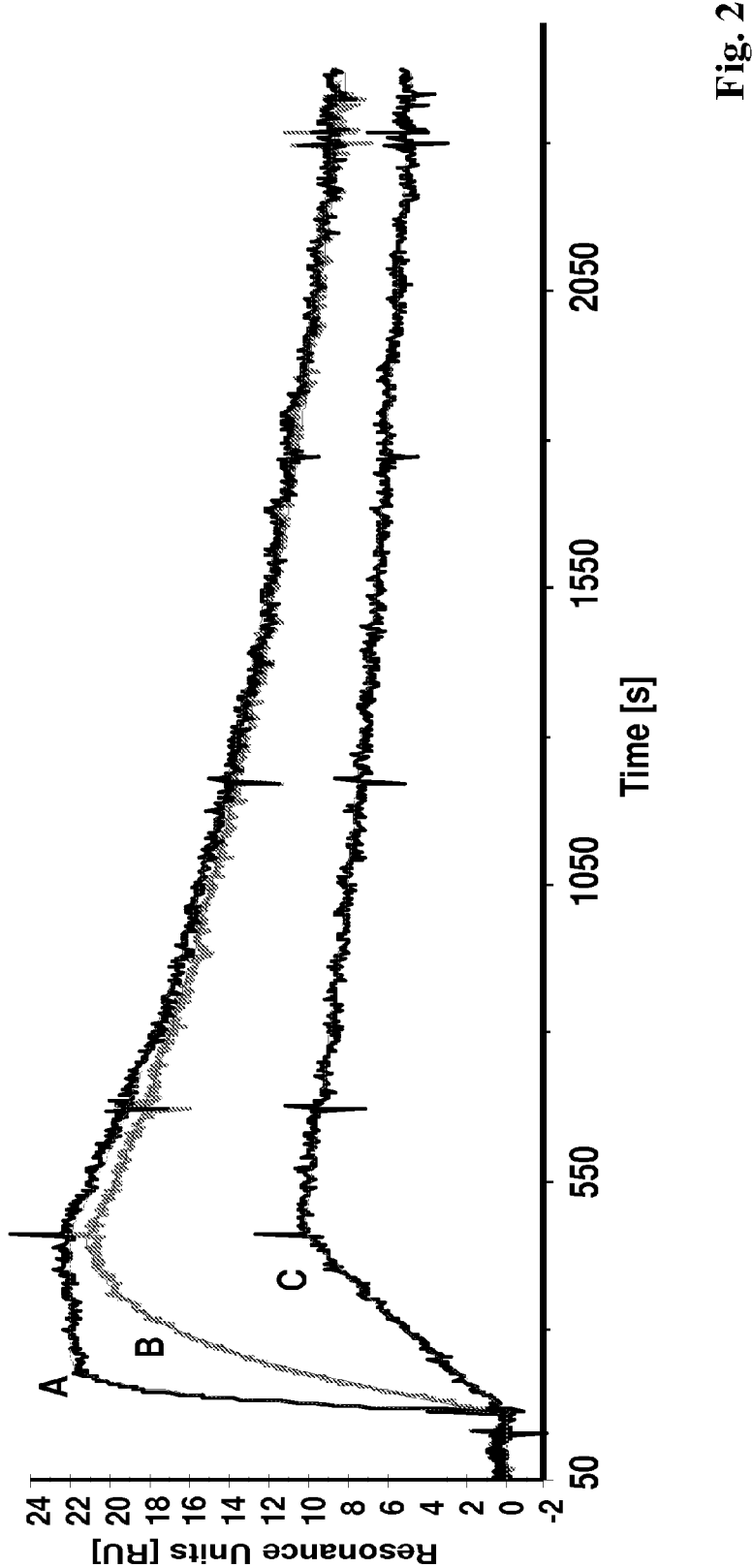
FIG. 2 shows Biacore sensorgrams obtained after injection of A: 6 nM; B: 1.5 nM and C, 0.38 nM of Affibody® molecule II (SEQ ID NO:5) with DOTA coupled to the C-terminal Cysteine over a sensor chip having HER2/Fc chimeric fusion protein immobilized thereto.
Figure 3:
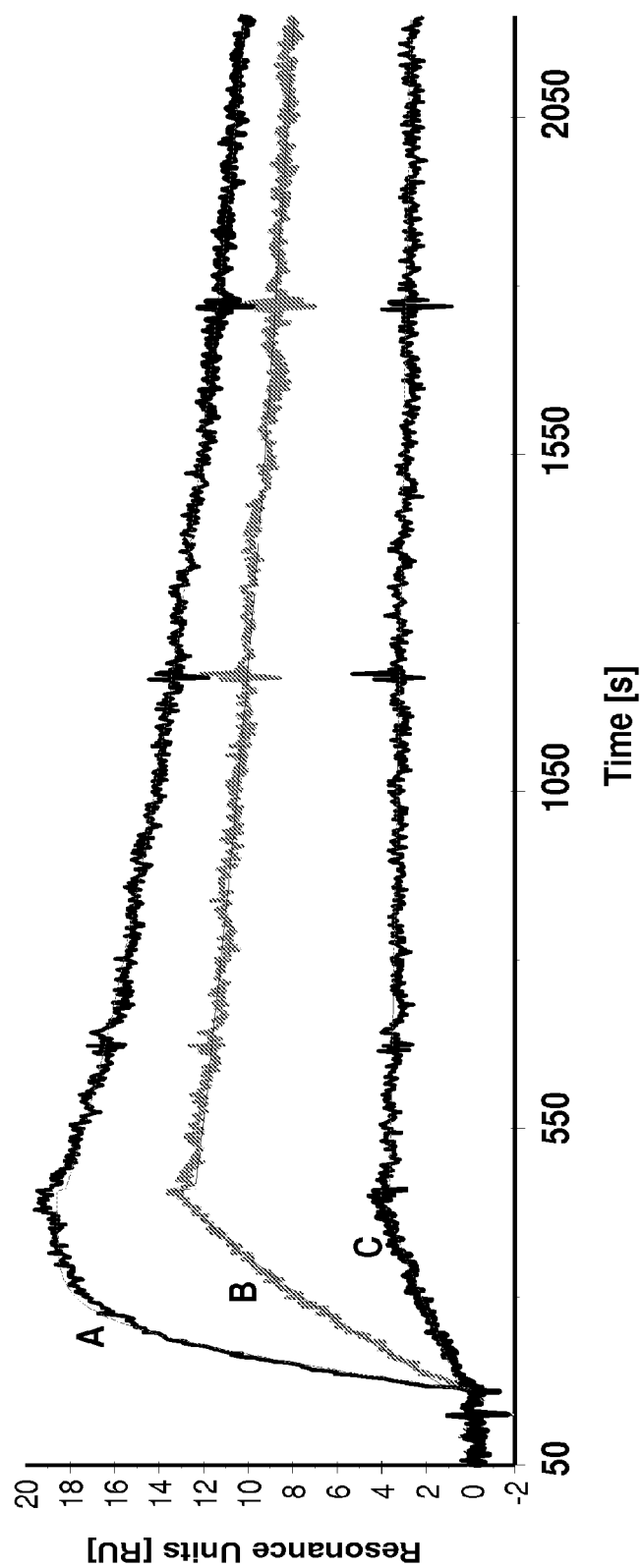
FIG. 3 shows Biacore sensorgrams obtained after injection of A: 6 nM; B: 1.5 nM and C, 0.38 nM of Affibody® molecule X (SEQ ID NO:7) over a sensor chip having HER2/Fc chimeric fusion protein immobilized thereto.

The HER2-binding interaction of the Affibody® molecule II is shown in the sensorgraphs of FIG. 1, Affibody® molecule II with DOTA coupled to the C-terminal cysteine in FIG. 2 and of the Affibody® molecule X (SEQ ID NO:7) in FIG. 3.

A kinetic study was performed to determine the binding parameters for the interaction of the Affibody® molecules with the HER2 target. Three different concentrations of the Affibody® molecules were injected over Biacore chip surfaces with immobilized HER2/Fc chimeric fusion protein. The dissociation equilibrium constants ($K_D=k_d/k_a$), the association rate constants ($k_a$) and the dissociation rate constants ($k_d$) are summarized in Table 2. DOTA coupling to the C-terminal cysteine did not significantly change the $K_D$ compared with the NEM-blocked Affibody® molecule II.

TABLE 2

|  | ka (1/Ms) | kd (1/s) | $K_D$ (pM) |
|---|---|---|---|
| Affibody ® molecule II (SEQ ID NO: 5) with NEM | 1.23E+07 | 7.41E−04 | 60 |
| Affibody ® molecule II (SEQ ID NO: 5) with DOTA | 1.27E+07* | 8.10E−04* | 65*† |
| Affibody ® molecule X (SEQ ID NO: 7) | 6.72E+07 | 5.57E−04 | 83 |

*mean of 18 determinations
†±8.66 (STDEV)

Example 3a

In Vivo HER2 Binding Properties of Polypeptides According to the Invention Having a Polyaminopolycarboxylate Chelator Summary In the experiments making up this example the binding of radiolabeled polypeptides according to the invention were analyzed in vivo in a mouse xenograft model. Affibody® molecule II with DOTA coupled to the C-terminal cysteine was radiolabeled with $^{111}$In and injected into mice bearing HER2 overexpressing SKOV-3 tumor xenografts and in HER2 negative A431 tumor xenografts as control. Biodistribution and gamma camera imaging studies were performed to analyze the distribution of the radiolabeled Affibody® molecule to different organs and localization in the whole animal.

[111]In labeling

The Affibody® molecule II was modified by coupling mono-amide DOTA (Mal-DOTA) to the C-terminal cysteine as described in example No. 2. The resulting molecule is named "Affibody® molecule II with DOTA".

For $^{111}$In labeling 30 µg of the Affibody® molecule II with DOTA (in 30 µl ammonium acetate buffer pH 5.5) were mixed with 40.5 µl stock solution of [111]InCl$_3$ (15 MBq on the time of labeling). The pH of the reaction mixture was ~5.0. The reaction mixture was incubated at 60° C. for 60 min.

The labeling efficiency was analyzed by instant thin layer chromatography (ITLC) on Silica gel impregnated glass fiber sheets (ITLC SG sheets, Gelman Sciences Inc.) using 0.02 M citric acid as eluent. The distribution of the radioactivity along ITLC strip was visualized and quantified using a PhosphorImager (Cyclone™ Storage Phosphor System, Packard). Radiolabeled Affibody® molecules remained at the origin of the ITLC sheet, whereas free $^{111}$In migrated with the solvent front.

The radiochemical purity was 99.8-99.9%, i.e. the radiolabeling was nearly quantitative. No further purification of the radiolabeled Affibody® molecule was required. The reaction mixture was diluted with PBS to 1.4 ml and kept frozen before the experiment (1-2 days).

Tumor Model

Female outbred BALB/c nu/nu mice were grafted with 1×10$^7$ SKOV-3 (human ovary ascites adenocarcinoma) cells or 1×10$^7$ A431 (human epidermoid carcinoma) cells in the right hind leg. SKOV-3 cells overexpress HER2 and A431 cells are negative for HER2.

Biodistribution in Tumor Bearing Mice

For the biodistribution studies, mice bearing xenograft tumors (30-40 days after implantation of 1×10$^7$ SKOV-3 cells) were randomized in groups of four. Mice were injected in the tail vein with 1 µg (100 kBq) of $^{111}$In-labeled Affibody® molecule in 100 µl PBS. All injections were tolerated well. One group of animals were s.c. injected with 1.5 ml (0.9 mg) of unlabeled Affibody® molecule II wherein the C-terminal Cys had been blocked with NEM as described in example 2 followed by i.v. injection with 1 µg (100 kBq) of $^{111}$In-labeled Affibody® molecule 50 min later (blocking experiment).

After injection of a lethal dose of a solution of Ketalar and Rompun solution, mice were sacrificed by exsanguinations via heart puncture at 0.5, 1, 4 and 24 hours post injection (h p.i.). Animals from the blocking group were sacrificed 4 hours p.i. The organs were dissected, weighted and their radioactivity content was measured in the gamma counter. Radioactivity uptake was calculated as percent of injected activity per gram tissue (% IA/g).

Imaging

For the gamma camera imaging, mice bearing xenograft tumors (30-40 days after implantation of 1×10$^7$ SKOV-3 cells or 10-15 days after implantation of 1×10$^7$ A431 cells) were used.

Mice were injected in the tail vein with 3 µg (4.5 MBq) of $^{111}$In-labeled Affibody® molecule II in 100 µl PBS. 0.5 or 4 hours p.i., the animals were euthanized with a lethal dose of a solution of Ketalar and Rompun. Imaging was performed using a Millenium GE gamma-camera equipped with a MEGP collimator. The scintigraphic results were evaluated visually using the Hermes software (Nuclear Diagnostics, Stockholm, Sweden).

Results

Figure 4:
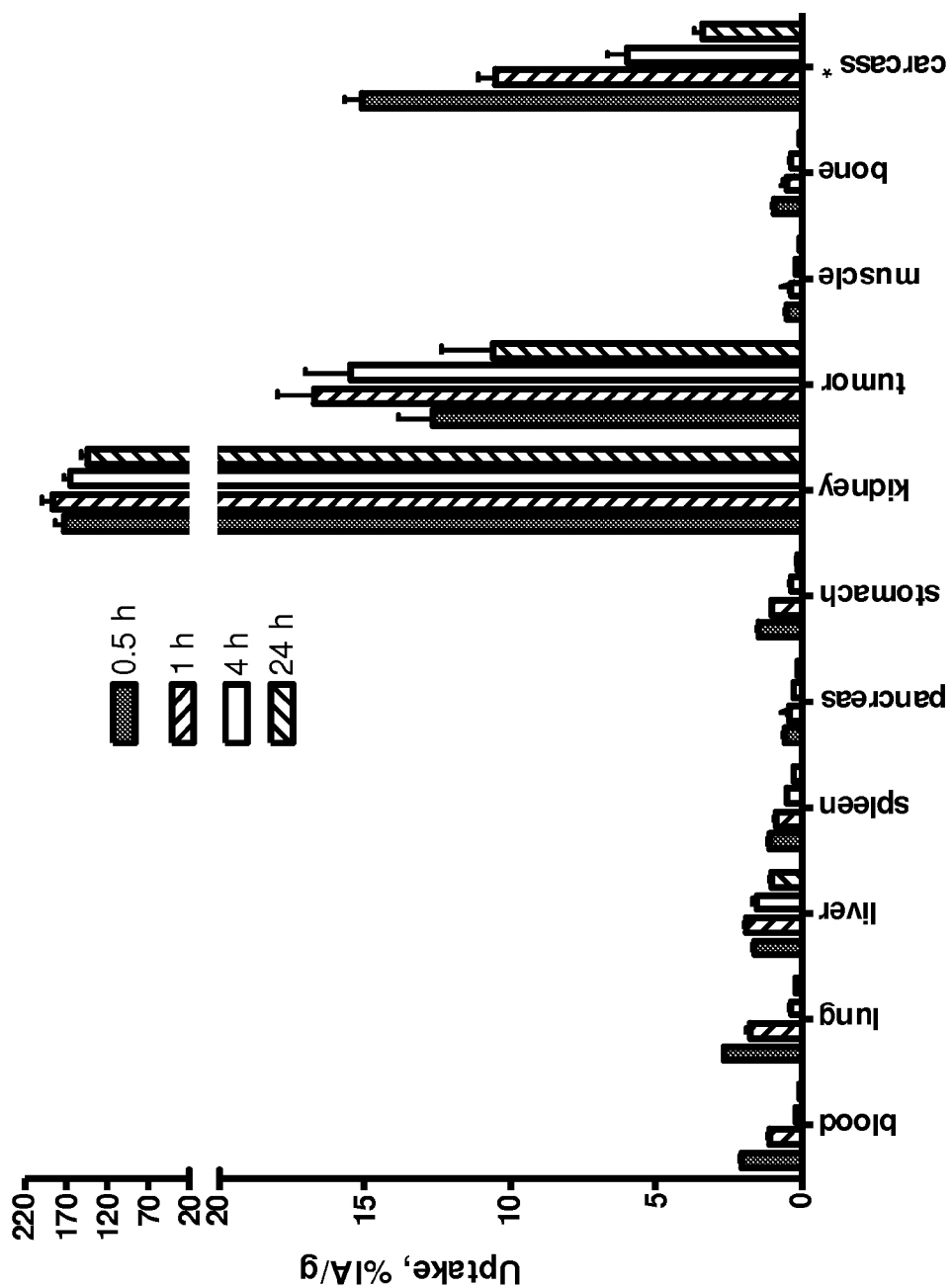
FIG. 4 shows the biodistribution of $^{111}$In-labeled Affibody® molecule II with DOTA in BALB/c nu/nu mice SKOV-3 tumor xenografts. All mice were injected with 1 μg (100 kBq) of $^{111}$In-labeled Affibody® molecule II. 0.5, 1, 4 and 24 hours post injection the organs were dissected, weighted and their radioactivity content was measured in the gamma counter. Radioactivity uptake was calculated as percent of injected activity per gram tissue (% IA/g).
Figure 5:
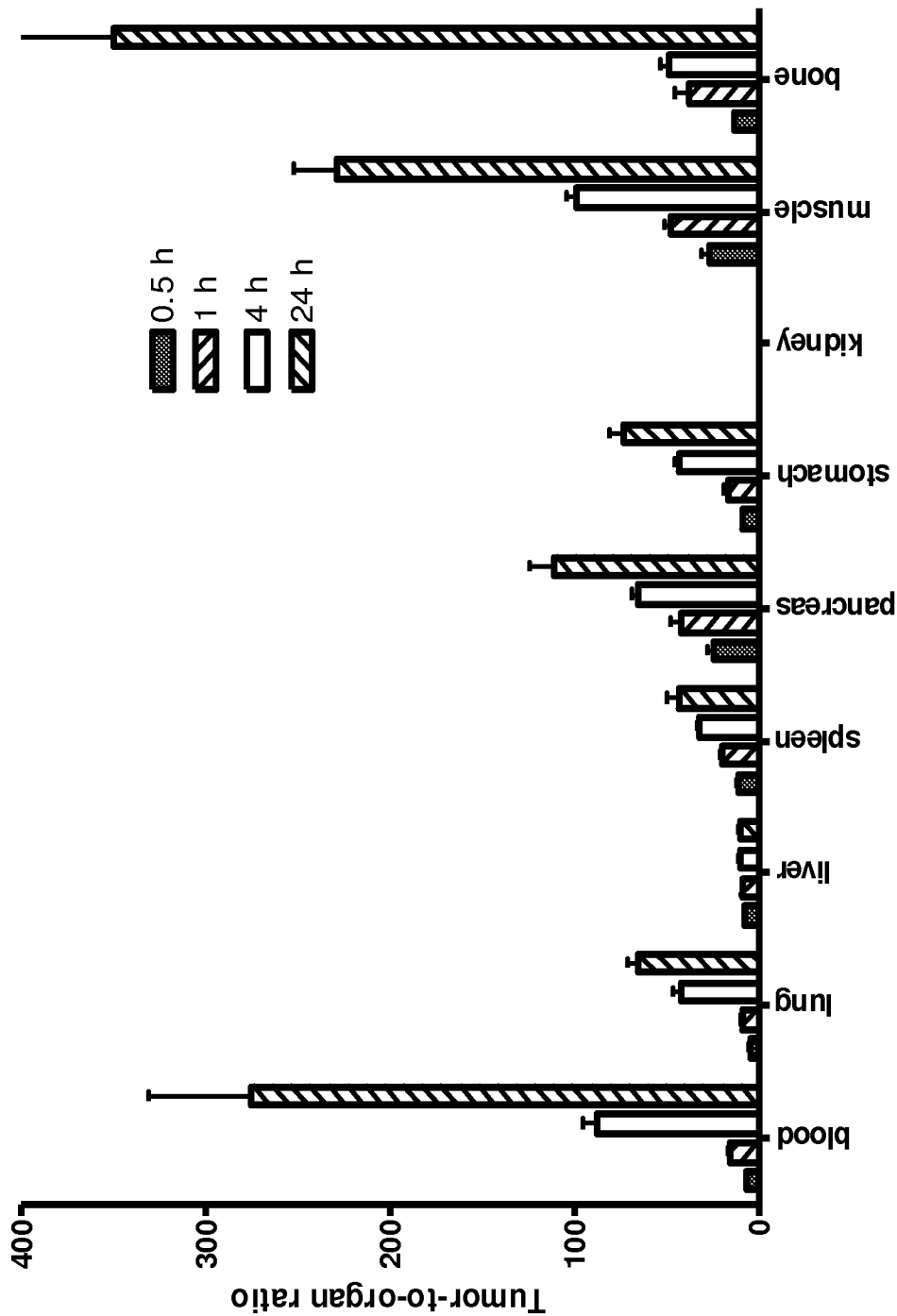
FIG. 5 shows the tumor-to-organ ratios of the radioactive uptake measured in the biodistribution study described in FIG. 4.

The results from the biodistribution study using $^{111}$In-labeled Affibody® molecule II with DOTA is shown in FIG. 4. Uptake of radioactivity at all time points was higher in the tumor than in all other organs, apart from kidney. Tumor uptake was 13±2% IA/g already at 0.5 hour p.i., increased to 17±2% IA/g at 1 hour p.i. and decreased slowly from 15±3% IA/g at 4 hours p.i. to 11±4% IA/g at 24 hours p.i. A high uptake of radioactivity was also found in kidneys, which is expected since kidneys are the main excretion pathway for small proteins as the Affibody® molecules. The highest kidney uptake with 186±24% IA/g measured at 1 hour p.i.

decreased to 144±13% IA/g at 24 hours p.i. Thus, the kidney uptake was considerable lower than the kidney uptake measured for the Affibody® molecule Z00342 (disclosed in WO 2005/003456 as $Z_{HER2:107}$, and sometimes also called $Z_{HER2:342}$) with DOTA coupled to the N-terminus, i.e. 243±22% IA/g measured at 1 hour p.i. and 232±34% IA/g at 24 hours p.i. (Orlova, A. et al. (2006), Cancer Research 67: 2178-2186). In addition, the $^{111}$In-labeled Affibody® molecule II with DOTA had lower uptake in all organs at all measured time points compared with the HER2-specific Affibody® molecule described by Orlova, et al. (2006). The high tumor uptake together with reduced uptake in other organs lead to tumor-to-organ ratios, which exceed the ratios published for the Affibody® molecule described earlier (FIG. 5). For example, the tumor-to-blood ratio was 16 at 1 hour p.i., 88 at 4 hour p.i. and 275 at 24 hours p.i. compared with 8 (1 h p.i.), 12 (4 h p.i.) and 47 (24 h p.i.) for the Affibody® molecule described by Orlova, A. et al. (2006).

Figure 6:
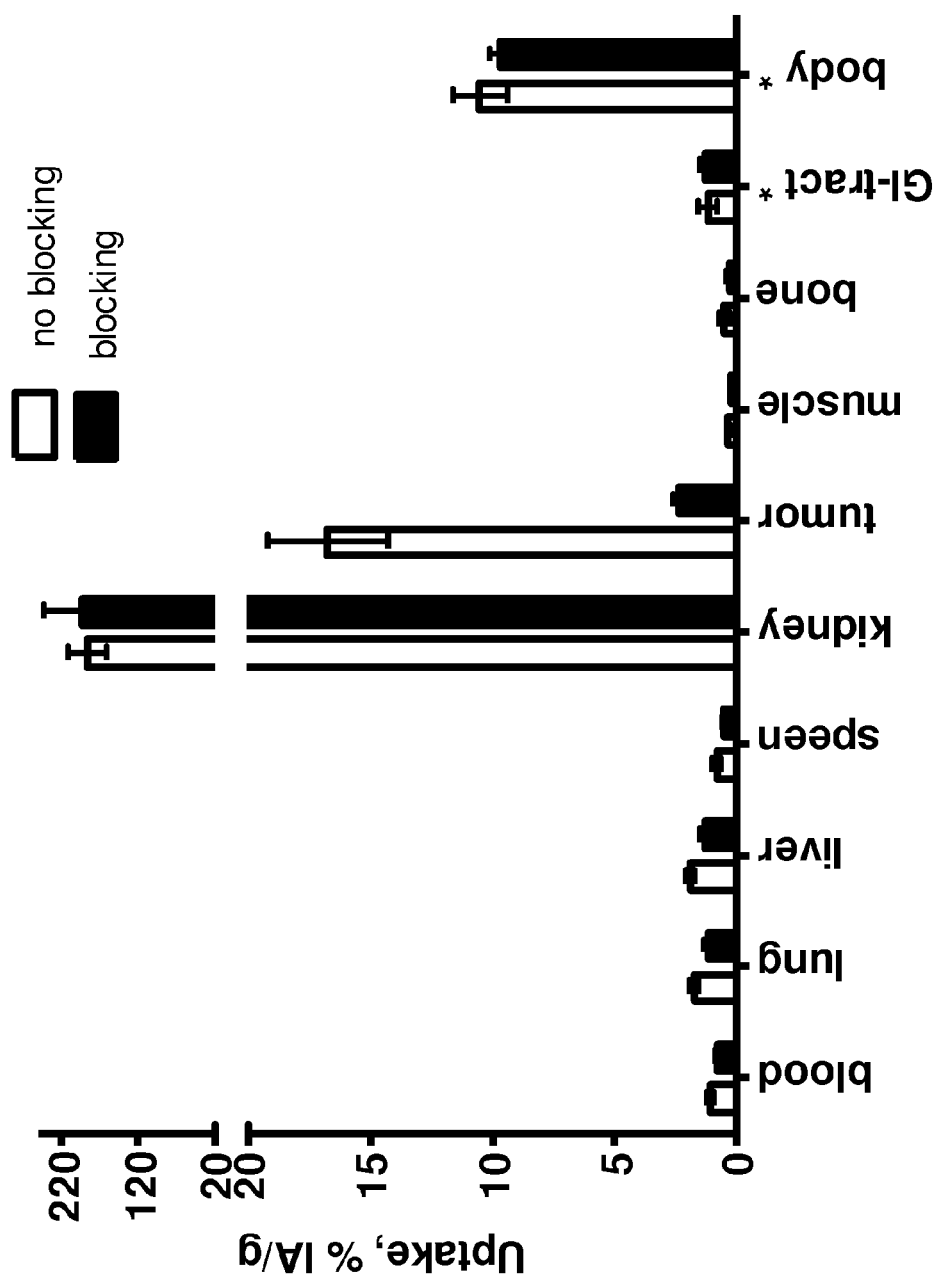
FIG. 6 shows the specificity of tumor targeting with $^{111}$In-labeled Affibody® molecule II with DOTA in SKOV-3 tumor xenografts. All mice were injected with 1 μg (100 kBq) of $^{111}$In-labeled Affibody® molecule II with DOTA. One group of animals was pretreated with excess of unlabeled Affibody® molecule (blocking group) 50 minutes before injection of the $^{111}$In-labeled Affibody® molecule. The organs were dissected 4 hours post injection, weighted and their radioactivity content was measured in the gamma counter. Radioactivity uptake was calculated as percent of injected activity per gram tissue (% IA/g).
Figure 7:
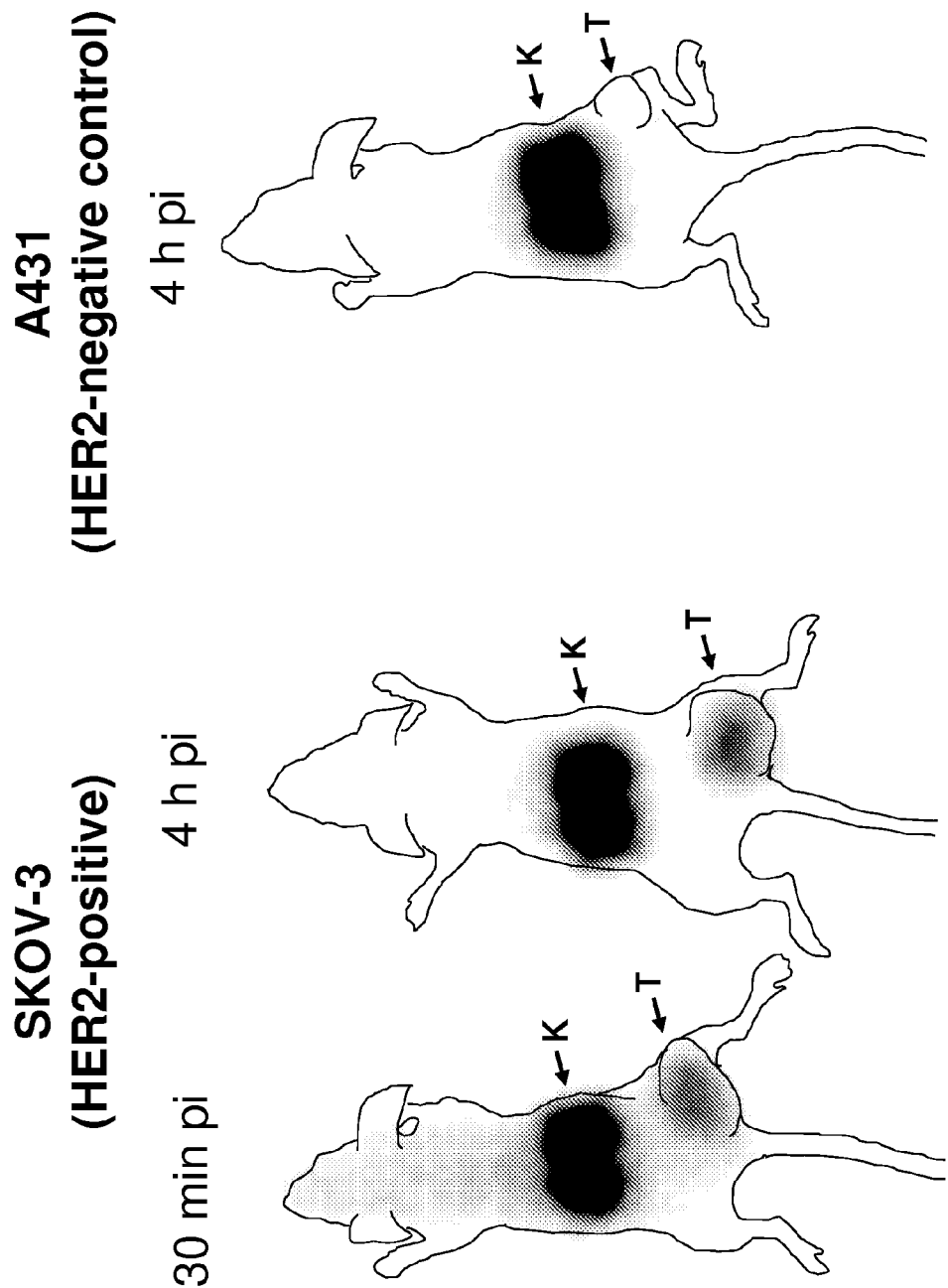
FIG. 7 shows gamma camera images of HER2 expressing SKOV-3 xenograft tumors in BALB/c nu/nu mice (left part, 30 minutes and 4 h p.i.) and HER2 negative A431 xenografts (right part, 4 h p.i.). All mice were injected with 3 μg (4.5 MBq) of $^{111}$In-labeled Affibody® molecule II with DOTA. K=kidney, T=tumor.

The specificity of tumor targeting using the Affibody® molecules according to the invention was proven by a blocking experiment, where pre-injection of tumor bearing mice with excess of unlabeled Affibody® molecule reduced tumor uptake of $^{111}$In-labeled Affibody® molecule II with DOTA by 86% but not the uptake in other organs (FIG. 6). Gamma camera images taken 30 minutes and 4 hours p.i. confirmed high specific tumor targeting of the $^{111}$In-labeled Affibody® molecule II with DOTA (FIG. 7). The SKOV-3 tumors were visualized already 0.5 hours p.i., and at 4 hours p.i. the background radioactivity was washed out. Apart from the tumor a clear uptake is also visible in the kidneys. The mouse bearing the HER2-negative A431 xenograft tumor had negligible uptake of the radioactivity in the tumor at 4 h p.i.

Example 3b

In Vivo HER2 Binding Properties of Polypeptides According to the invention having a $N_3S$ Chelator Summary In the experiments making up this example the binding of radiolabeled polypeptides according to the invention were analyzed in vivo in a mouse xenograft model. Affibody® molecule X (SEQ ID NO:7) containing an N-terminal mercaptacetyl-glutamyl-seryl-glutamyl (ma-ESE) sequence was radiolabeled with $^{99m}$Tc and injected into mice bearing HER2 overexpressing SKOV-3 tumor xenografts. Biodistribution and gamma camera imaging studies were performed to analyze the distribution of the radiolabeled Affibody® molecule to different organs and localization in the whole animal.

$^{99m}$Tc Labeling

Affibody® molecule X was labeled with $^{99m}$Tc using the indirect method.

For labeling with $^{99m}$Tc, a kit containing the following ingredients was produced: 50 mg gluconate dihydrate, 1 mg disodium salt of EDTA and 0.5 mg tin (II) chloride dihydrate per 1 ml. The solution was divided into aliquots containing 1 ml, and aliquots were freeze-dried. Freeze-dried labeling kits were stored at −20° C. before use.

50 µl PBS (2.68 mM KCl, 137 mM NaCl, 1.47 mM $KH_2PO_4$, 8.1 mM $Na_2HPO_4$, pH 7.4) was added to 50 µg ABY-024 solution (2 mg/ml in deionized degassed water). After vortexing, the mixture was mixed with a technetium labeling kit, and 200 µl of $^{99m}TcO_4$-containing eluate from a $^{99m}$Tc generator (UltratechneKow FM generator, Tyco Healthcare Nordic AB, Mallinckrodt Sweden AB) was added. The mixture was incubated at 90° C. for 60 min Two small (0.8 µl) aliquots of each mixture were applied to two ITLC SG strips and one was eluted with PBS (to determine yield) and another with mixture of pyridine:acetic acid: water (5:3:1.5) (to determine the presence of reduced hydrolyzed technetium (RHT)). In this eluent, the technetium colloids remained at the origin, while the radiolabeled Affibody® molecules, pertechnetate and other complexes of $^{99m}$Tc migrated with the solvent front. The distribution of the radioactivity along ITLC strip was visualised and quantified using a PhosphorImager (Cyclone™ Storage Phosphor System, Packard). Labelling was nearly quantitative, which made any additional purification unnecessary.

The radiolabeled Affibody® molecule was diluted with PBS to ensure that radioactivity concentration is 65 kBq per 100 µl. The concentration of Affibody® molecules was adjusted to 1 µg per 100 µl.

Biodistribution in Tumor Bearing Mice

Female outbred BALB/c nu/nu mice were grafted with $1 \times 10^7$ SKOV-3 (human ovary ascites adenocarcinoma) cells in the right hind leg.

For the biodistribution studies, mice with xenograft tumors (40-45 days after implantation of $1 \times 10^7$ cells) were randomized in groups of four.

Mice were injected in the tail vein with 1 µg (65 kBq) of $^{99m}$Tc-labeled Affibody® molecule X in 100 µl PBS. All injections were tolerated well. One group of animals were s.c. injected with 100 µl (0.5 mg) of unlabeled $His_6$-Z00342 by i.v. injection with 1 µg (65 kBq) of $^{99m}$Tc-labeled Affibody® molecule X 50 min later (blocking experiment).

After injection of a lethal dose of a solution of Ketalar and Rompun, mice were sacrificed by exsanguinations via heart puncture at 4 hours post injection (h p.i.). Animals from the blocking group were sacrificed 4 hours p.i. The organs were dissected, weighted and their radioactivity content was measured in the gamma counter. Radioactivity uptake was calculated as percent of injected activity per gram tissue (% IA/g).

Imaging

For the gamma camera imaging, mice bearing xenograft tumors (40 days after implantation of $1 \times 10^7$ SKOV-3 cells or 10-15 days after implantation of $1 \times 10^7$ A431 cells) were used.

Mice were injected in the tail vein with 3 µg (15 MBq) of $^{99m}$Tc-labeled Affibody® molecule X in 100 µl PBS. 1 or 4 hours p.i., the animals were euthanized with a lethal dose of a solution of Ketalar and Rompun. Imaging was performed using a e. Cam Siemens gamma-camera equipped with a LEHR collimator. The scintigraphic results were evaluated visually using the Hermes software (Nuclear Diagnostics, Stockholm, Sweden).

Results

Figure 8:
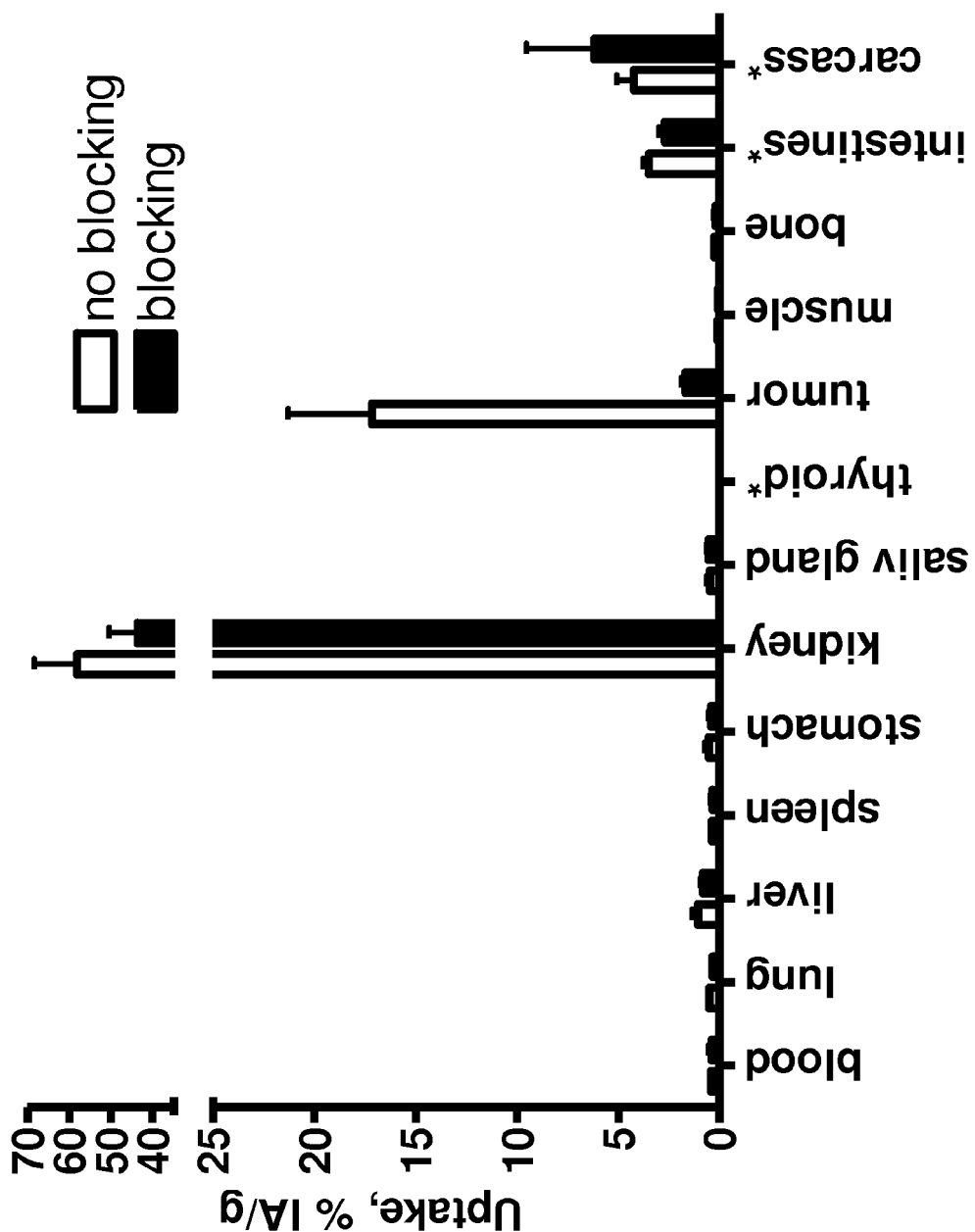
FIG. 8 shows the biodistribution of $^{99m}$Tc-labeled Affibody® molecule X in BALB/c nu/nu mice SKOV-3 tumor xenografts 4 hours post injection. All mice were injected with 1 μg (65 kBq) of $^{99m}$Tc-labeled Affibody® molecule X. One group of animals was pretreated with excess of unlabeled Affibody® molecule (blocking group) 50 minutes before injection of the $^{99m}$Tc-labeled Affibody® molecule. The organs were dissected 4 hours post injection, weighted and their radioactivity content was measured in the gamma counter. Radioactivity uptake was calculated as percent of injected activity per gram tissue (% IA/g).

The results from the biodistribution study using $^{99m}$Tc-labeled Affibody® molecule X is shown in FIG. 8. Uptake of radioactivity at 4 h p.i. was higher in the tumor than in all other organs, apart from kidney. Tumor uptake was 17±4% IA/g at 4 hours p.i. A high uptake of radioactivity was also found in kidneys, which is expected since kidneys are the main excretion pathway for small proteins as the Affibody® molecules. The kidney uptake was with 58±10% IA/g measured at 4 hour p.i. Thus, the kidney uptake was considerable lower than the kidney uptake measured for the $^{111}$In-labeled Affibody® molecule described in example 3a above and Z00342 with DOTA coupled to the N-terminus (Orlova, A. et al. (2006), Cancer Research 67: 2178-2186). In addition, low uptake in intestine (3.52% IA/g) and liver (1.06% IA/g) together with the higher uptake in the kidneys show that the $^{99m}$Tc-labeled Affibody® molecule X is predominantly cleared by the renal pathway and not by the hepatobiliary pathway. EP 6 123 095 discloses that the preferred ma-Xaa1-Xaa2-Xaa3 chelating moiety comprising one or two Ser and the remaining two or one amino acid residues being Glu result in a shift from hepatobiliary to renal clearance pathway. Affibody® molecule X contains both one of the preferred chelator moieties disclosed in EP 6 123 095, i.e. ma-Glu-Ser-Glu and the all of the amino acid exchanges described in Example 1 (table 1) of the current invention which result in increased hydrophilicity of these polypeptides. Thus, the $^{99m}$Tc-labeled Affibody® molecule X described here represents an additional example of a polypeptide containing a ma-Xaa1-Xaa2-Xaa3 chelating moiety which balance low hepatobiliary clearance with high renal clearance, but minimized re-absorption in the kidneys.

The uptake of $^{99m}$Tc-labeled Affibody® molecule X in all organs was similar to the uptake of $^{111}$In-labeled Affibody® molecule described in example 3a.

Figure 9:
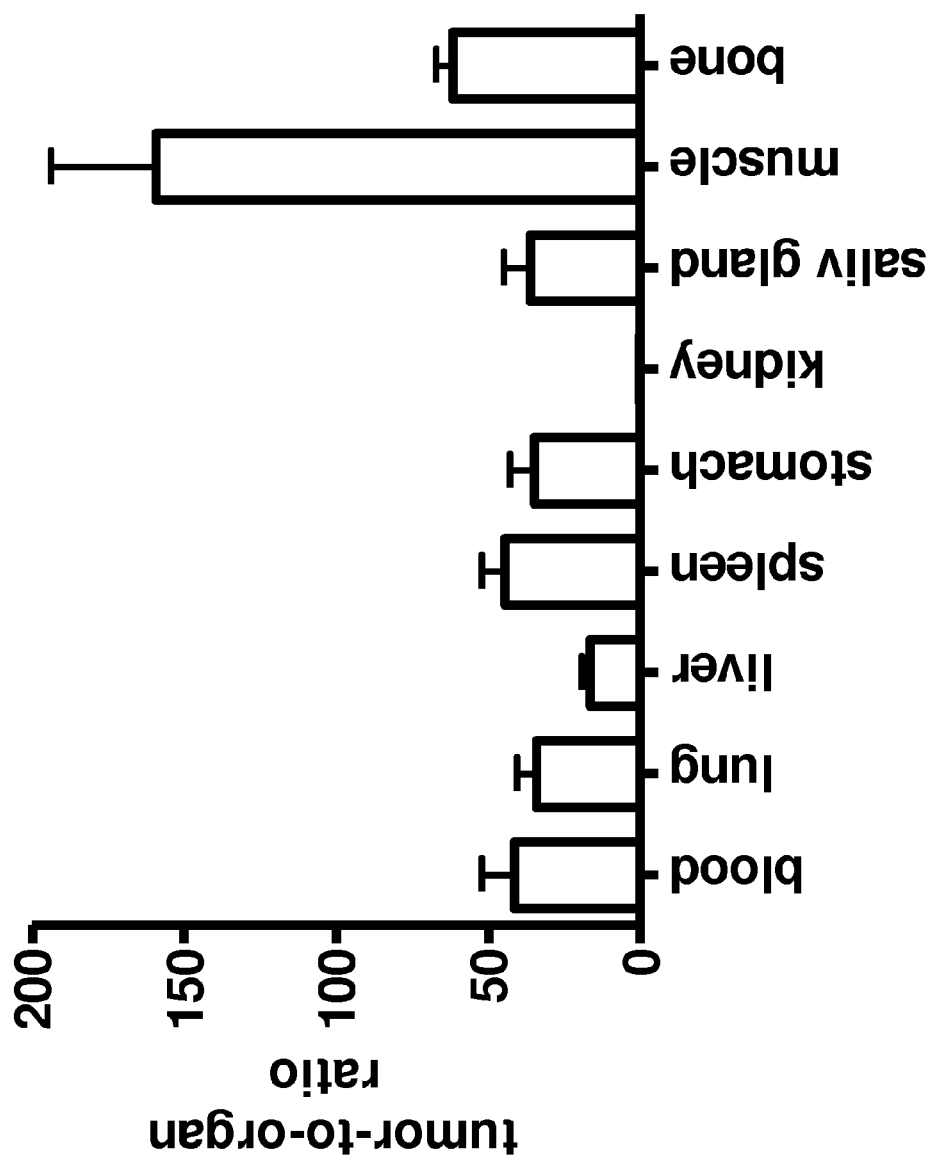
FIG. 9 shows the tumor-to-organ ratios of the radioactive uptake measured in the biodistribution study described in FIG. 8.

The tumor-to-organ ratios of the biodistribution experiment described above are shown in FIG. 9. Again high tumor-to-organ ratios were obtained. In particular the tumor-to-liver ratio of the $^{99m}$Tc-labeled Affibody® molecule X was 17 compared with the $^{111}$In-labeled Affibody® molecule II with DOTA described in example 3a with a ratio of 10 at 4 hours p.i. The tumor-to-blood ratio was 42 at 4 hours p.i.

The specificity of tumor targeting using the Affibody® molecule X was proven by a blocking experiment, where pre-injection of tumor bearing mice with excess of unlabeled Affibody® molecule reduced tumor uptake of $^{99m}$Tc-labeled Affibody® molecule X by 90% but not the uptake in other organs (FIG. 8).

Figure 10:
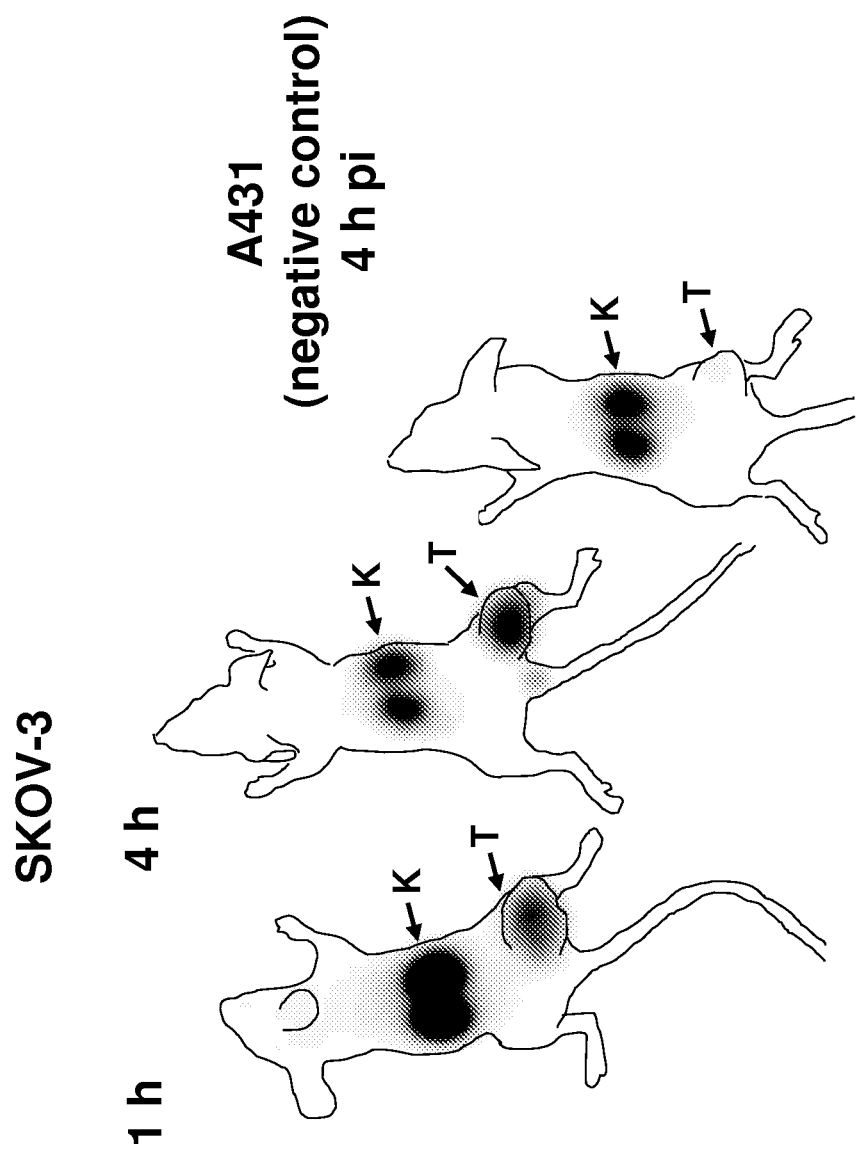
FIG. 10 shows gamma camera images of HER2 expressing SKOV-3 xenograft tumors in BALB/c nu/nu mice (left part, 1 h and 4 h p.i.) and HER2 negative A431 xenografts (right part, 4 h p.i.). All mice were injected with 3 μg (15 MBq) of $^{99m}$Tc-labeled Affibody® molecule X. K=kidney, T=tumor

Gamma camera images taken 1 hour and 4 hours p.i. confirmed high specific tumor targeting of the $^{99m}$Tc-labeled Affibody® molecule according to the invention (FIG. 10). The SKOV-3 tumors were visualized already 1 hour p.i., and at 4 hours p.i. the background radioactivity was washed out. Apart from the tumor a clear uptake is also visible in the kidneys, however this uptake was considerably lower compared with the kidney uptake of the $^{111}$In-labeled Affibody® molecule II with DOTA described in example 3a. The mouse bearing the HER2-negative A431 xenograft tumor had negligible uptake of the radioactivity in the tumor at 4 h pi.

Example 4

Comparative Study of Chemical Synthesis of a Polypeptide According to the Invention and of Z00342

Summary

In the experiments making up this example solid phase peptide synthesis of polypeptides according to the invention is described. The mutations introduced at four positions, i.e. [N23T], [A42S], [A46S] and [A54S] allowed for using an alternative synthesis strategy with pseudoproline precursors with the simplified abbreviation Fmoc-Xxx-Yyy-OH. Using pseudoprolines in the four positions described above made it possible to synthesize the whole Affibody® molecule X (SEQ ID NO:7) (i.e. aminoacids 1-58) whereas standard synthesis failed to produce the peptide.

The introduction of novel serine or threonine residues also enables the use of isoacyl dipeptides, which is an alternative to pseudoprolines for increasing the synthetic efficiency by reducing aggregation during peptide synthesis (Sohma et al., Tetrahedron Lett. 47:3013, 2006). Several such building blocks are available from Novabiochem of MerckBiosciences AG.

Rationale

Peptide synthesis of the Affibody® molecule Z00342 (disclosed in WO 2005/003156 as $Z_{HER2:107}$, and sometimes also called $Z_{HER2:342}$) as well as coupling of DOTA to the N-terminus for this Affibody® molecule is possible and described in the literature (Orlova, A et al. (2006), Cancer Research 67: 2178-2186). However, a huge variation in peptide yield after synthesis was observed. The difficulties to reproducibly synthesize the peptide can be both related to the length of the peptide as well as the primary amino acid sequence. In addition long peptides with the reactive groups of the amino acid side chains still protected may generate unfavorable secondary structures, e.g. beta sheets which can disturb solid phase peptide synthesis (Quibell, M. & Johnson, T., in Fmoc Solid Phase Peptide Synthesis-A Practical Approach, W. C. Chan, P. D. White Eds, Oxford University Press 2000, 115-135). One way to prevent secondary structure formation during peptide synthesis is the use of pseudoprolines. Peudoprolines with the simplified abbreviation Fmoc-Xxx-Yyy-OH can be used if the amino acid Yyy is serine, threonine or cysteine. These pseudoprolines display a closed proline-like structure with the side chain linked to the backbone, and which can be converted into the normal amino acid structure by acid treatment (Haack, T., & Mutter, M. Tetrahedron Letters (1992), 33(12), 1589-92). Pseudoprolines are commercially available for 14 amino acids in position Xxx (except Arg, Cys, H is, Met, Pro, Thr) together with serine or threonine in position Yyy.

The parent Affibody® molecule Z00342 has no threonine and cysteine in the primary sequence. Serine is only found in position 33, 39 and 41. A pseudoproline precursor is only available for serine 41 ($Q^{40}$-$S^{41}$) For the two other serines the amino acid in position Xxx prevents the use of pseudoprolines since there are no precursors available ($R^{32}$—$S^{33}$ and $P^{38}$—$S^{39}$).

The mutations introduced in the polypeptides according to the invention are aimed, but are not restricted to, to facilitate peptide synthesis. Especially the mutations in position 23, 42, 46 and 54, i.e. [N23T], [A42S], [A46S] and [A54S] may have the capacity to solve two of the problems in SPPS identified: they allow the use of psudeoprolines and the critical region around amino acid 21 to 26 is changed in position 23 by replacing asparagine with threonine.

Solid Phase Peptide Synthesis (SPPS)

The amino acid sequence of Affibody® molecule X (SEQ ID NO:7) was assembled on an Fmoc-Lys(Boc)-Wang polystyrene resin in a fully automated peptide synthesizer. This resin is highly suitable for the formation of peptides with the Fmoc-strategy. 57 Amino acids (with appropriate side-chain protection) were coupled onto the resin. In the last step coupling of S-trityl-protected mercaptoacetic acid was performed manually.

Step 1: Solid Phase Peptide Synthesis

The Fmoc-Lys(Boc)-Wang polystyrene resin was transferred into an SPPS-reactor with a stirrer. Synthesis was then started with Fmoc deprotection of the resin, followed by a coupling procedure with Fmoc-Pro-OH according to the general description given below. This step was again followed by an Fmoc deprotection and subsequent coupling of the amino acid derivatives according to the sequence. After final washings of the resin with isopropylether (IPE), the peptide resin was dried in a desiccator under reduced pressure.

Both a standard Fmoc peptide synthesis and a synthesis using pseudoprolines in four positions were performed. For standard peptide synthesis only Fmoc-amino acids were used. For the alternative peptide synthesis apart from Fmoc-amino acids the following pseudoprolines were used: Fmoc- Leu-Thr-OH in position 22-23, Fmoc-Ser-Ser-OH in position 41-42, Fmoc-Leu-Ser-OH in position 45-46 and Fmoc-Asp-Ser-OH in position 53-54.

Fmoc Deprotecting Procedure

The resin was also treated with 20% piperidine in NMP in order to achieve the cleavage of the N-α-Fmoc protecting group. The washing of the resin was then performed with NMP.

Coupling Procedure

Automated coupling of the amino acid derivates Pro57 to Glu1. Up to 3 eq of the Fmoc-AA derivative were dissolved in NMP. For the coupling, 2-(1H-Benzotriazole-1-yl)-1,1,3,3-tetramethyluronium tetrafluoroborate (TBTU) in dimethyl-formamide (DMF) and sym.-collidine (2,4,6-trimethylpyridine) in NMP were added. The resulting solution was mixed at room temperature before it was poured onto the resin. NMP was used as solvent. After a coupling time of at least 15 minutes at 60° C., the resin was washed with NMP.

After each coupling procedure, a repetition of the coupling with 2-(1H-7-azabenzotriazol-1-yl)-1,1,3,3-tetramethyluronium tetrafluoroborate (TATU) in DMF as coupling reagent and with dichloroethane as solvent takes place automatically, followed by acetic anhydride capping.

Step 2 Coupling of Mercaptoacetic Acid

Acylations were performed with 5 molar equivalents amino acid, 2-(1H-benzotriazol-1-yl)-1,1,3,3-tetramethyluronium hexafluorphosphate (HBTU) and 1-hydroxybenzotriazole (HOBt) and 10 equivalents N-ethyldiisopropylamine (DIEA, from Lancaster Synthesis, Morecambe, England). S-Trityl-mercaptoacetic acid was from AnaSpec Inc (San Jose, Calif., USA).

Step 3: Cleavage from the Resin Including Cleavage of the Remaining Protection Groups The peptide resin was treated with trifluoroacetic acid (TFA) in the presence of purified water, ethanedithiol (EDT), and triisopropylsilane (TIS). After approx. 2 hours of cleavage time at room temperature, the reaction mixture was cooled to approx. 0° C., and ammonium iodide and dimethyl sulfide were added to reduce oxidized methionine. After an additional 60 min cleavage time at approx. 0° C., the formed iodine was reduced with ascorbic acid. After filtering off the product, it was precipitated in IPE in the cold, filtered off again, washed with IPE, and dried under reduced pressure.

Purity Analysis by HPLC

The purity of the 58 amino acid long peptides and some intermediates was determined by reversed phase HPLC using a Vydac 218 TP54 (5 µm, 250×4.6 mm) column and 0.1% TFA, 1% acetonitrile in H$_2$O and 0.1% TFA in acetonitrile as solvent A and B respectively. The column oven temperature was set to 35° C. The column was eluted either with a gradient of 15 to 45% solvent B in 30 minutes or with a gradient from 20 to 50% B in 30 minutes. UV detection was at 220 nm. The purity was calculated by area normalization.

Results

Figure 11:
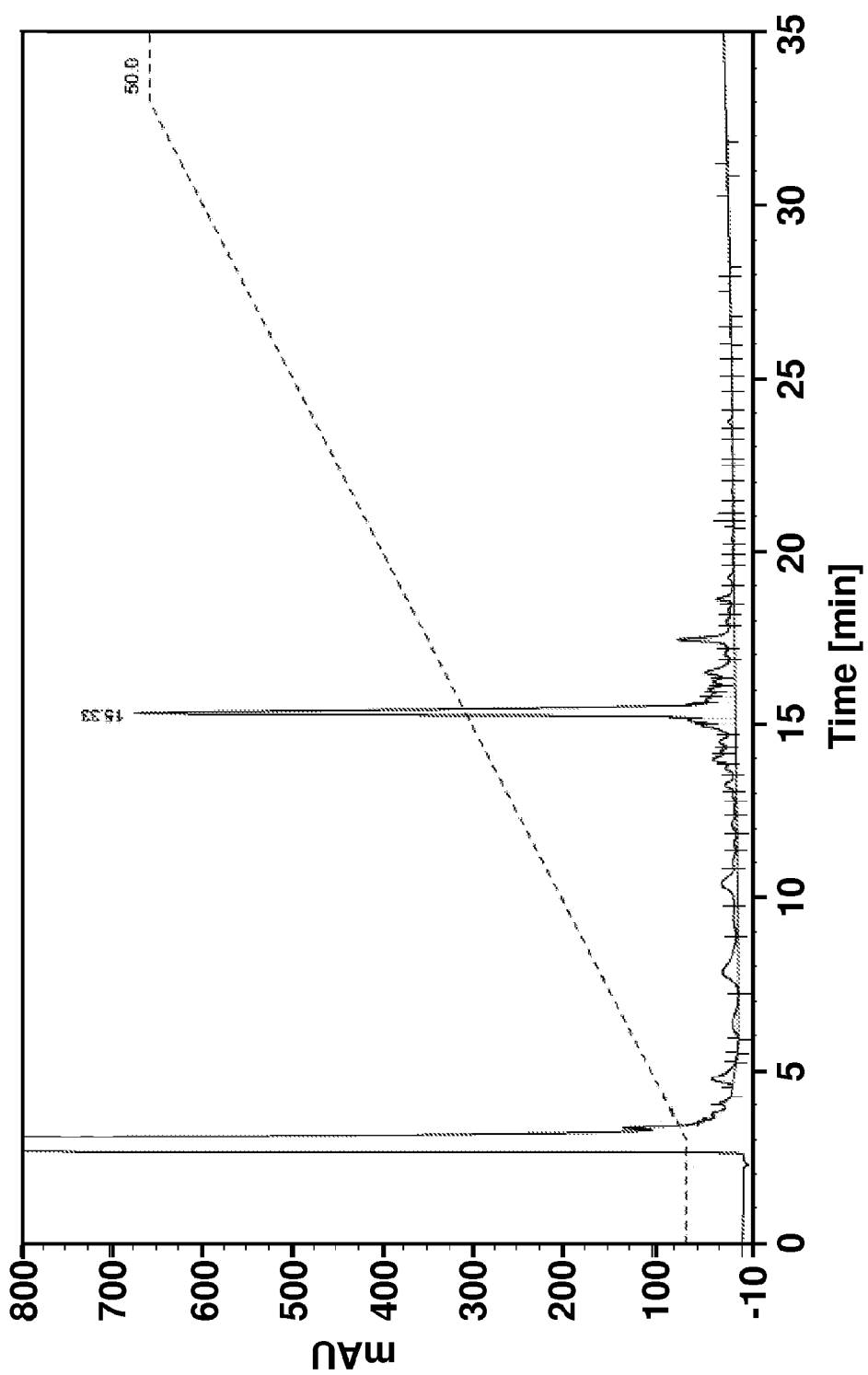
FIG. 11 shows the analytical HPLC elution profiles for Affibody® molecule X at the synthesis stage of amino acid 18 to 58. The Affibody® molecules were separated on a VydacTP218TP54 column. Flow rate: 1 ml/min; Temperature: 35° C.; Detection: 220 nm; Eluent A: 0.1% TFA, 1% acetonitrile in $H_2O$; Eluent B: 0.1% TFA in acetonitrile.
A) Synthesis performed on polystyrene resin using pseudoprolines in positions 22-23, 41-42, 45-46 and 53-54.
B) Standard peptide synthesis on polystyrene resin without pseudoprolines.
Figure 11:
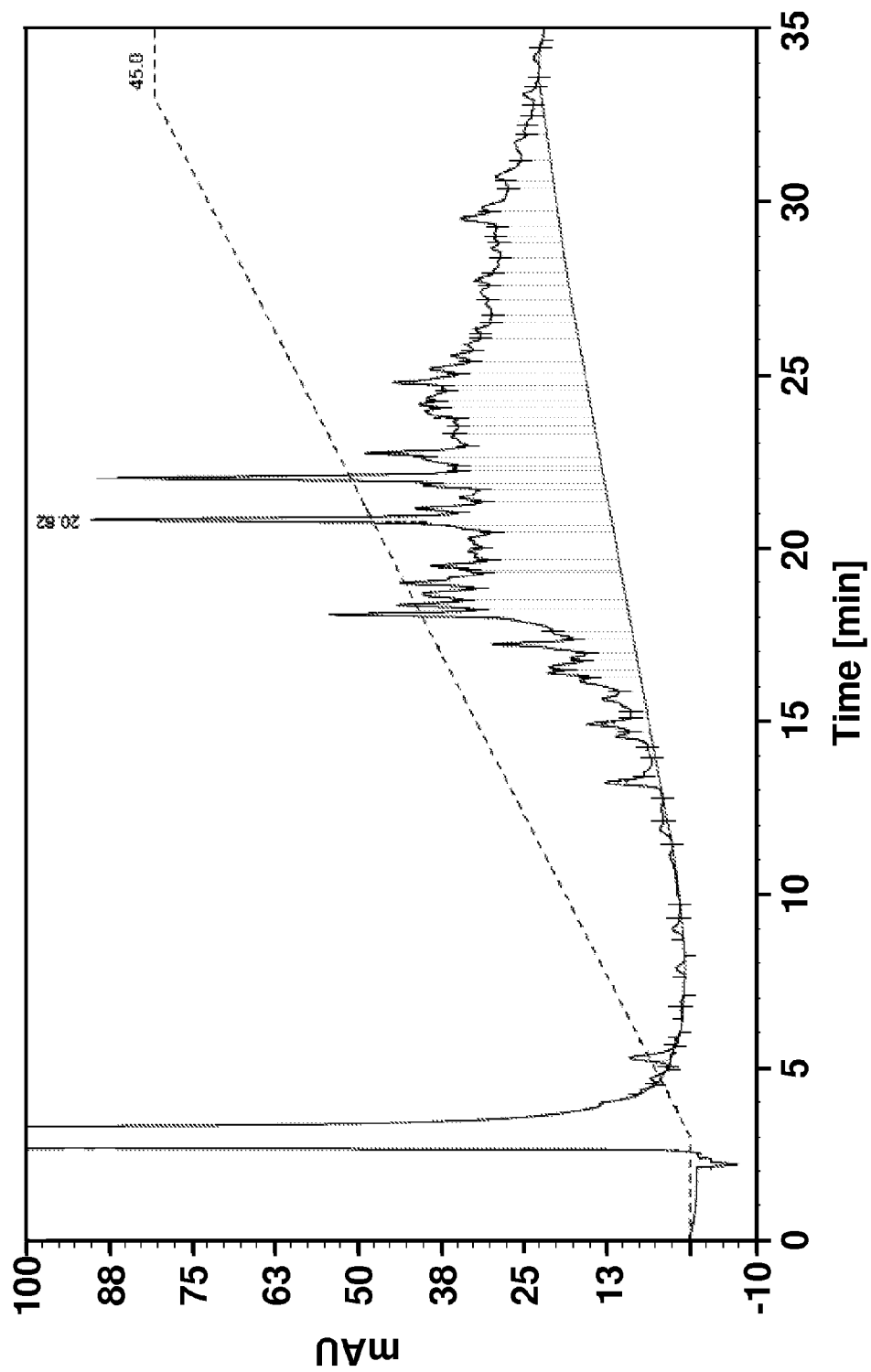
Figure 12:
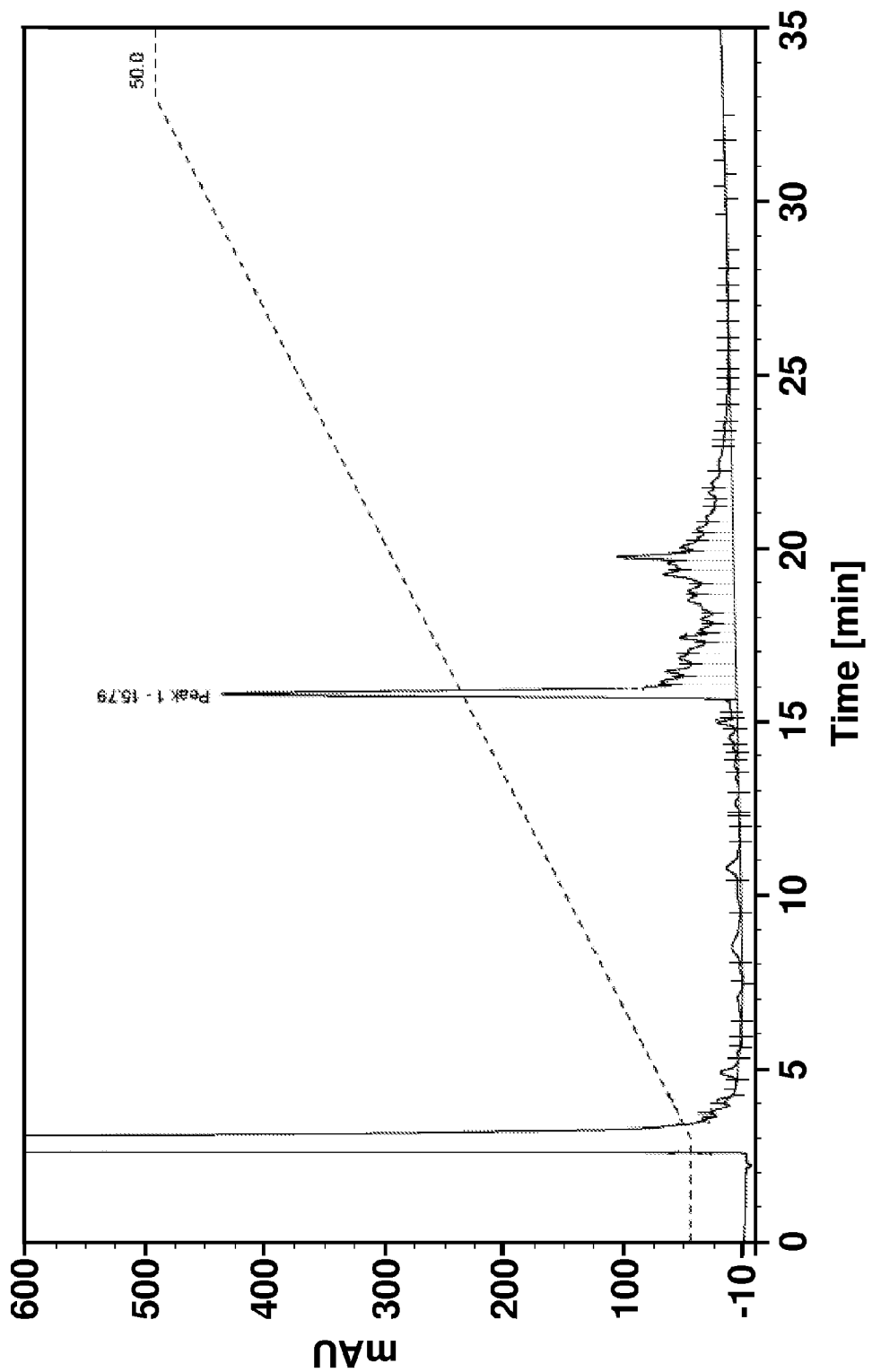
FIG. 12 shows the analytical HPLC elution profiles for the Affibody® molecule X at the synthesis stage of amino acid 1 to 58 (A) and 10 to 58 (B). The Affibody® molecules were separated on a VydacTP218TP54 column. Flow rate: 1 ml/min; Temperature: 35° C.; Detection: 220 nm; Solvent A: 0.1° A) TFA, 1% acetonitrile in $H_2O$; Solvent B: 0.1% TFA in acetonitrile.
A) Synthesis performed on polystyrene resin using pseudoprolines in positions 22-23, 41-42, 45-46 and 53-54.
B) Standard peptide synthesis on polystyrene resin without pseudoprolines.
Figure 12:
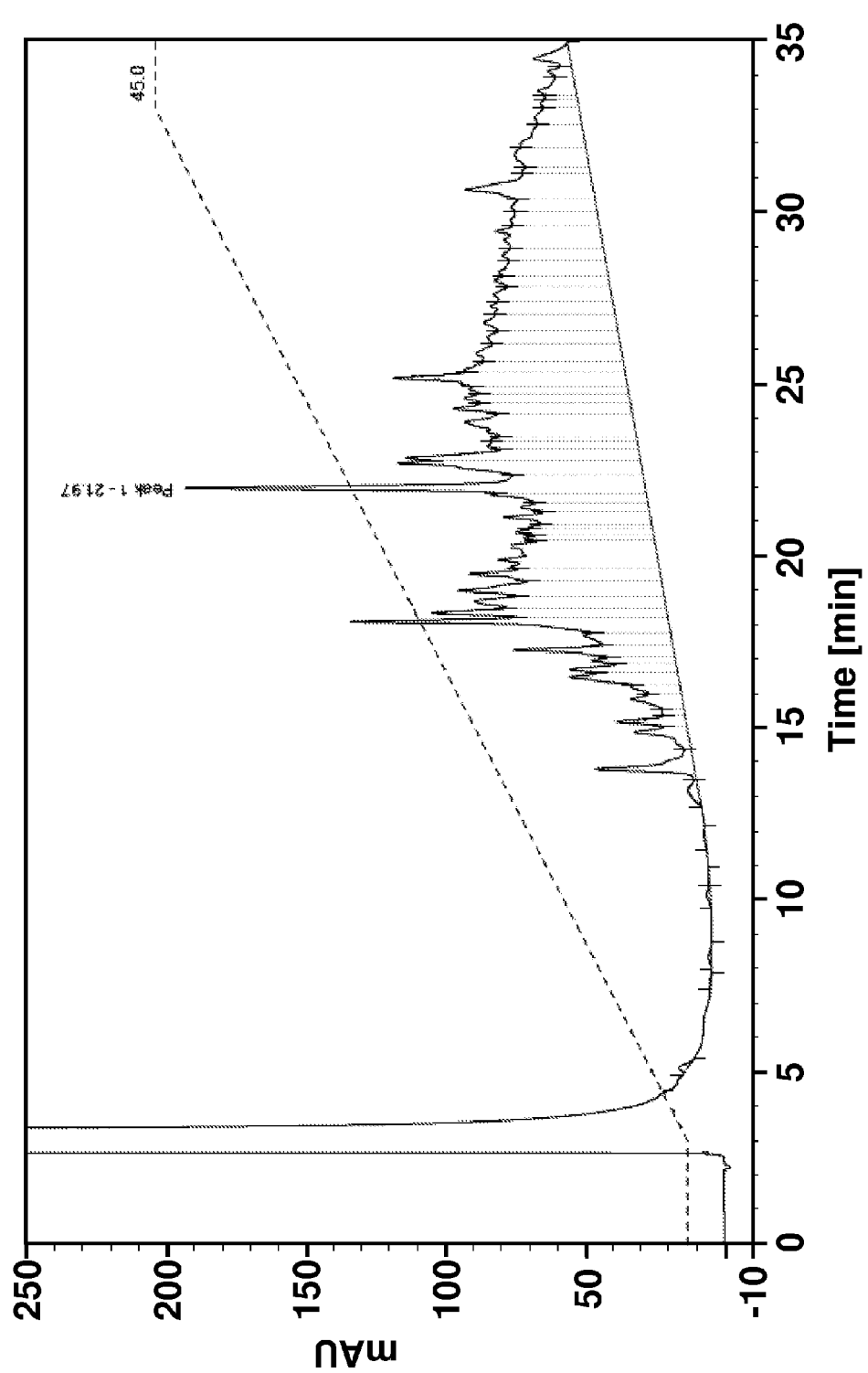

The yield and purity of Affibody® molecule X (SEQ ID NO:7), synthesized with or without the use of pseudoprolines were analyzed by analytical reversed phase chromatography. In order to follow the progress of the synthesis a small portion of synthesis resin was taken after several coupling steps and analyzed for the presence, purity and yield of the desired peptide intermediate. FIG. 11 shows the analysis of the 41 amino acid long peptide intermediate (amino acid 18-58). At this stage of the peptide synthesis one clear and predominant peptide peak with the right sequence (RT=15.33 min, yield 49%) was identified if the synthesis was performed using pseudoprolines (FIG. 11A). Standard Fmoc-synthesis, however, resulted in a huge number of small peptide peaks and two main peaks with similar size, but low yield. One of this two peaks (RT=20.82 min) was identified as the peptide intermediate with the right sequence (aa18-58) (FIG. 11B). The full length peptide (amino acids 1-58) was obtained only if the synthesis was performed using pseudoprolines. FIG. 12 A shows a single product peak with a yield of the final peptide of 26%. Standard Fmoc-synthesis, however, failed to produce the final peptide product. Analysis of the 49 amino acid long intermediate (amino acid 10-58) from the standard synthesis revealed that the desired intermediate could not be detected and the synthesis was aborted (FIG. 12 B).

Example 5

Comparative Study of Hydrophilicity of Polypeptide According to the Invention and of Z00342

Summary

In the experiments making up this example the increased hydrophilicity of the polypeptides according to the invention is described using two methods: 1) protein hydrophopicty/hydrophilicity plots of and 2) reversed phase HPLC elution profiles.

1) Protein Hydrophobicity/Hydrophilicity Plots

Hydrophobicity/hydrophilicity plots are generated to display the distribution of polar and apolar residues along a protein sequence. These plots are commonly used to predict highly hydrophobic regions, e.g. membrane-spanning parts or hydrophilic sequences, i.e. regions that are likely exposed on the surface of proteins.

The plots are generated by scanning the protein sequence with a moving window which can be adapted for the purpose of the analysis. For example a moving window of seven amino acids is suggested to be a good value for finding putative surface-exposed regions. At each position, the mean hydrophobic index of the amino acids within the window is calculated. This value is plotted as the midpoint of the window. For the hydrophobicity/hydrophilicity plots making up this example two hydrophobicity scales were used: 1) Kyte-Doolittle scale were hydropathic regions achieve a positive value (Kyte J., Doolittle R. F. (1982) J. Mol. Biol. 157:105-132) and 2) Hydrophobicity indices at pH 3.4 determined by HPLC (Cowan R., Whittaker R. G. (1990) Peptide Research 3:75-80). The plots were generated using the program Bio-Annotator which is a component of Vector NTI Suite 9.0.0. (Invitrogen)

Ten to twelve amino acids of the Affibody® molecule, i.e. amino acids not involved in target binding activity of the molecule (apart from one, Met$^9$) were changed when possible to more hydrophilic amino acids and/or to amino acids that reduce the overall antigenicity, to optimize the sequence for expression in *E. coli* and for labeling with radio nuclides.

Figure 13A:
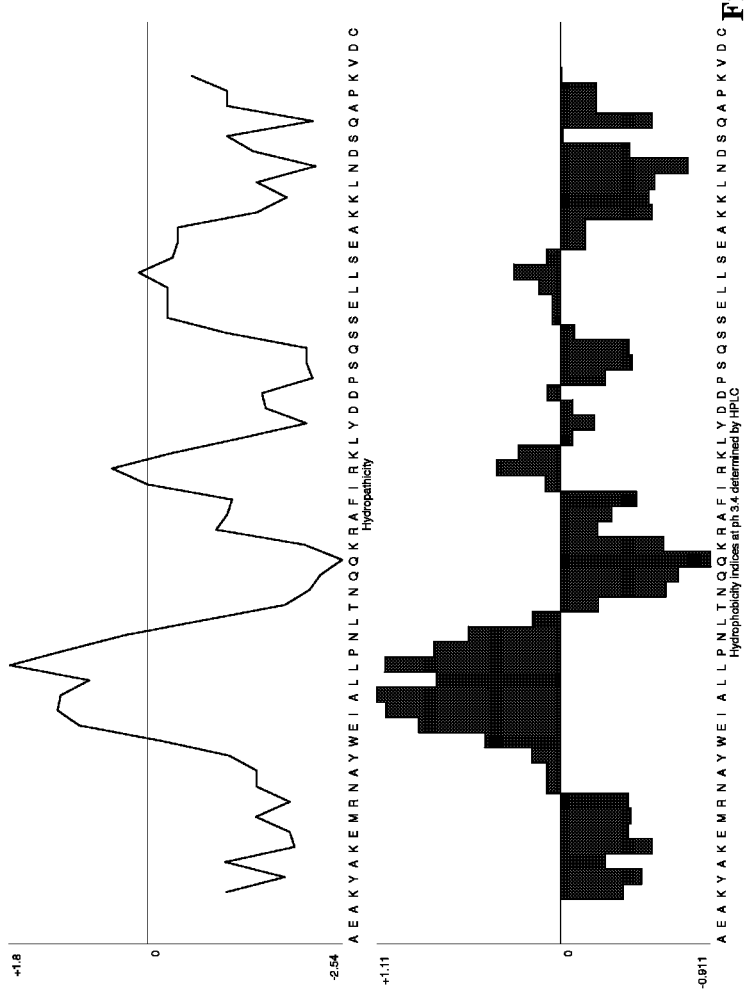
FIG. 13 shows hydrophobicity/hydrophilicity plots for some of the Affibody® molecules listed in Table 1. A) plot for Affibody® molecule II (SEQ ID NO:5), B) plot for Affibody® molecule with SEQ ID NO:X (SEQ ID NO:7) and C) plot for Affibody® molecule Z00342, the parent Affibody® molecule without mutations as control. The upper part of the figures shows the plot using the Kyte-Doolittle scale and the lower part the hydrophobicity indices at pH 3.4 determined by HPLC. Hydrophobic amino acids have positive values and hydrophilic amino acids have negative values. A moving window of seven amino acids was used for both plots. In B) only the amino acid sequence of Affibody® molecule X (SEQ ID NO:7), i.e. the Affibody® molecule X without ma was used to prepare the plots.
Figure 13B:
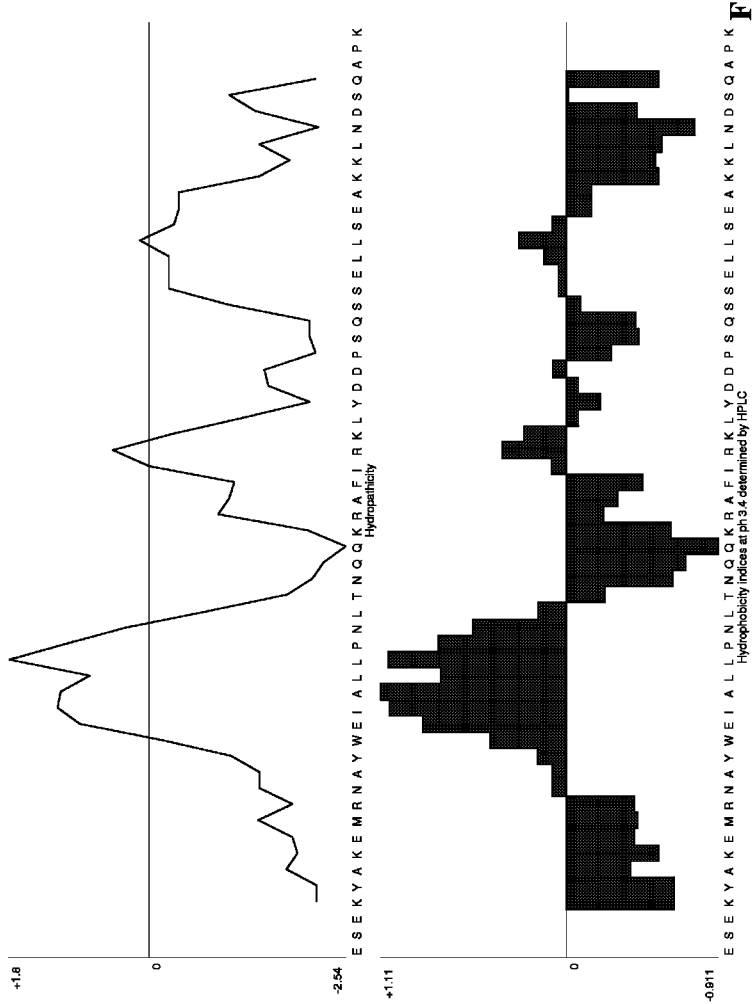
Figure 13C:
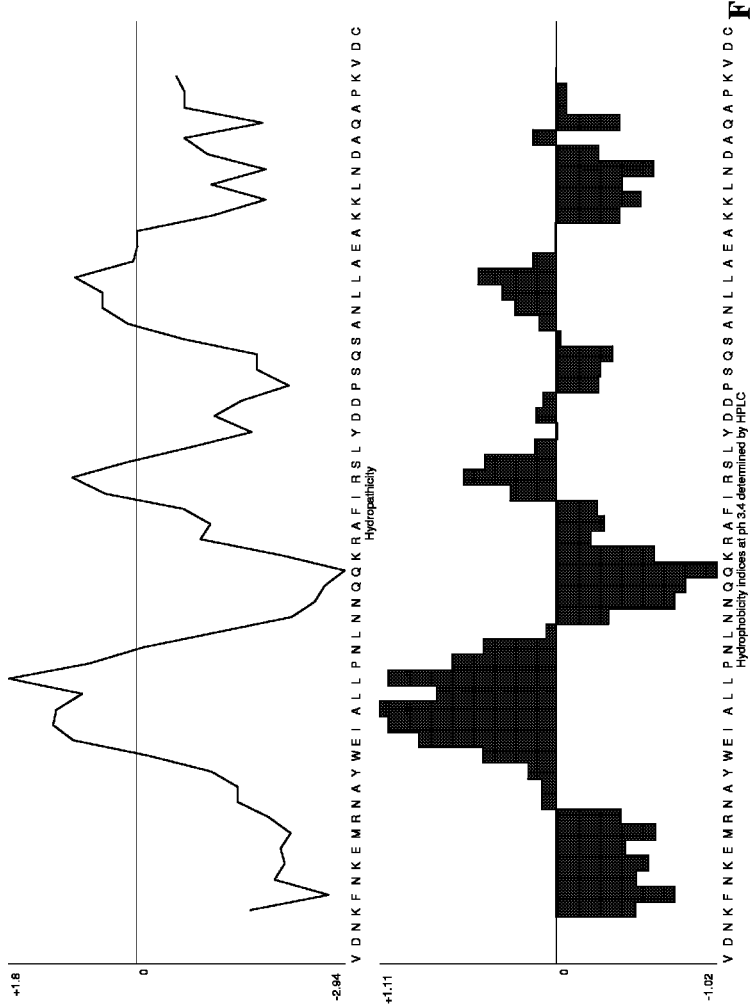

Two examples of hydrophobicity/hydrophilicity plots for polypeptides according to the invention are shown in FIGS. 13 A and B. For comparison the plot for the parent Affibody® molecule Z00342 is given in FIG. 13 C.

In the sequence of Affibody® molecule II (SEQ ID NO:5) the following amino acid changes were made:
- Four of these mutations exchanged nonpolar hydrophobic amino acids to polar amino acids [F5Y], [A42S], [A46S] and [A54S]
- Two which changed polar amino acid to non-polar hydrophobic amino acid [N3A] and [N6A]
- One which changed an uncharged polar amino acid to positive charged polar amino acid [S33K]

One which changed a polar amino acid to a negatively charged amino acid [N43E]

One which changed a polar amino acid to a less polar amino acid [N23T]

One which changed a nonpolar hydrophobic amino acid to a less hydrophobic amino acid [V1A]

One which changed a negatively charged amino acid to another negatively charged amino acid [D2E].

The plots for Affibody® molecule II in FIG. 13 A show increased hydrophilicity in the region of the Affibody® molecules making up the alpha helix 2 and 3 and the C-terminus (between amino acids 24-58) compared with the parent Affibody® molecule Z00342 (FIG. 13 C).

In the sequence of Affibody® molecule X (SEQ ID NO:7) the same amino acid changes were made as for Affibody® molecule II, but the first 3 amino acids where changed to more hydrophilic amino acids:

One of these mutations exchanged a nonpolar hydrophobic amino acid to a negatively charged amino acid [V1E]

one which changed a negatively charged amino acid to a polar amino acid [D2S]

one which changed an uncharged polar amino acid to negative charged polar amino acid [N3E]

The plots for Affibody® molecule X (SEQ ID NO:7) in FIG. 13 B show the same increased hydrophilicity in the region of alpha helix 2 and 3 (between amino acids 24-58) and a even more hydrophilic N-terminus compared with the parent Affibody® molecule Z00342 (FIG. 13 C).

2) Reversed Phase HPLC Elution Profiles

Figure 14:
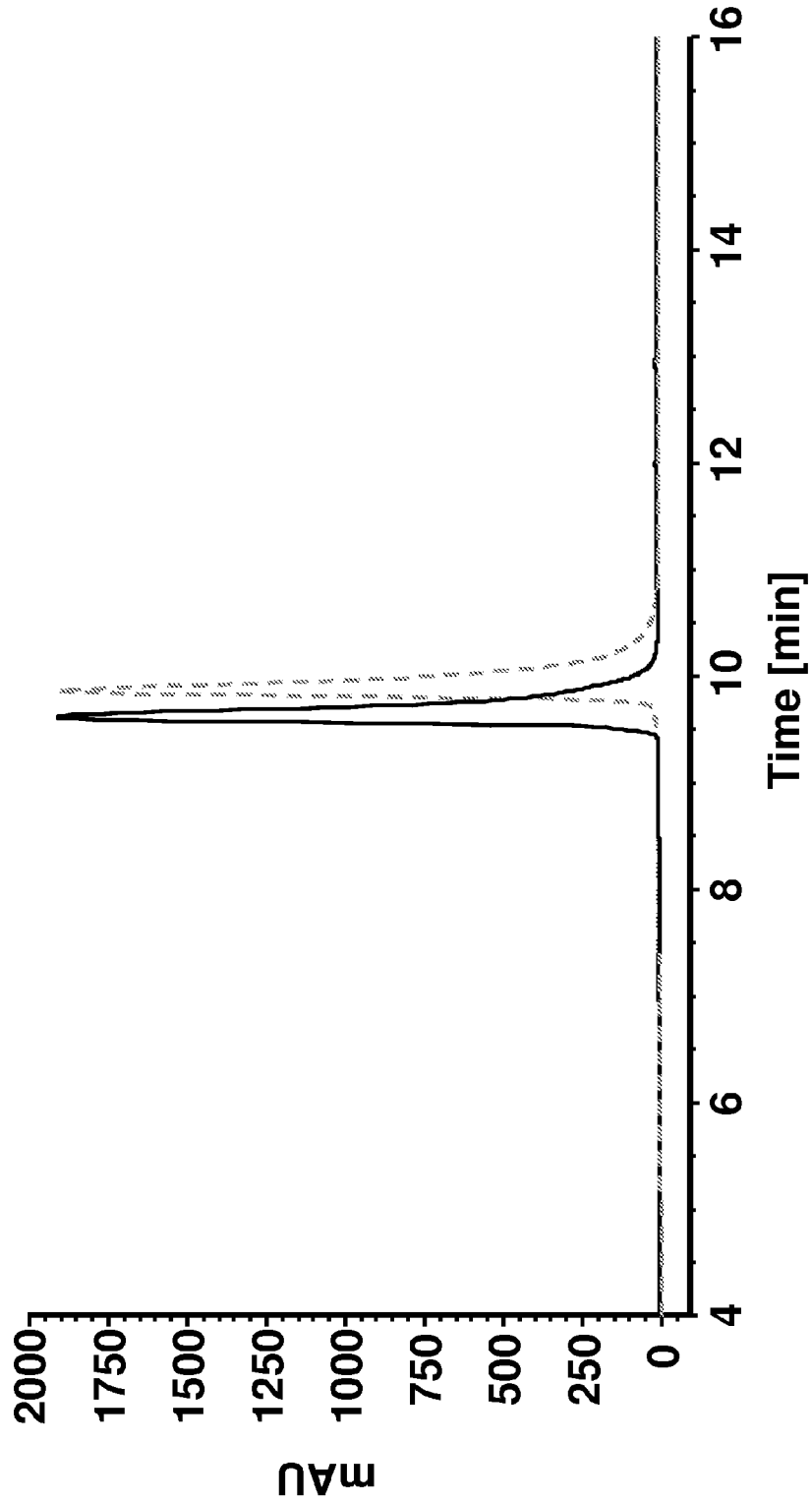
FIG. 14 shows the HPLC elution profiles for the Affibody® molecule II according to the invention (black line) and Affibody® molecule Z00342 (grey dashed line). The Affibody® molecules were separated on a Zorbax 300SB C8 150×2.1 mm, 3.5 μm column using a flow rate of 0.5 ml/min and a TFA, water, acetonitrile solvent system.

Proteins can be efficiently separated by reversed phase (RP) chromatography. Differences in hydrophilicity/hydropobicity of a protein can be analyzed on RP columns e.g. C8 or C18 columns where more hydrophilic proteins elute earlier, i.e. at lower concentrations of the acetonitrile eluent than more hydrophobic proteins. The following conditions were used to compare the elution of the Affibody® molecule II (SEQ ID NO:5) and the parent Affibody® molecule Z00342: HPLC instrument: Agilent 1100 (Agilent); Column: Zorbax 300SB C8 150×2.1 mm, 3.5 μm (Agilent); Temperature: 30° C.; Load: 20 μl of protein solution with 2.2 mg/ml; Flow rate: 0.5 ml/min; Solvent A: 0.5% trifluoroacetic acid (TFA) in water; Solvent B: 90 acetonitrile, 0.5% TFA in water; Gradient: 0-2 min 10% B, 2-17 min 10-70% B, 17-18 min 70-100% B, 18-21 min 100% B, 21-22 min 100-10% B, 22-25 min 10% B. The results of the analysis are shown in FIG. 14. The shift in retention time illustrates the increased hydrophilicity of the Affibody® molecule II compared with the parent Affibody® molecule Z00342. This Affibody® molecule with all the mutations described above elutes with a retention time of 9.614 min compared with 9.860 for the parent Affibody® molecule Z00342.

Example 6

Comparative Study of Antigenicity (IgG Binding) of Polypeptide According to the Invention and of Z00342

Summary

One desirable property of the HER2 specific polypeptides described in this invention is to have a low antigenicity profile meaning to show low interaction potential with immunoglobulins (Ig). In this example, a method to measure antigenicity (IgG binding) in vitro is described, and Affibody® molecules I, II, II with DOTA conjugated to C-terminal cystein and XI with DOTA conjugated on an internal cystein (position 42) are compared with the standard HER2 specific Affibody® molecule Z00342 in order to evaluate the influence of the amino acid alterations made. The assay used is referred to as an in vitro antigenicity (IVA) ELISA.

In Vitro Antigenicity (IVA) ELISA

In the IVA ELISA, a 96 well plate was coated with 2 μg/ml of the HER2 specific Affibody® molecule Z00342, which was selected as the standard coating reagent. In addition, the plate was coated with 2 μg/ml of the HER2 specific Affibody® molecules I, II, II with DOTA and XI with DOTA. 50 μl of coating solution were added per well and the half-area plate was incubated at +4° C. over night. The ELISA plate was washed two times with tap water and 100 μl of blocking solution (phosphate buffered saline (PBS) pH 7.4 with 0.5% casein) were added to each well. The plate was subsequently incubated for 1 hour at room temperature (RT), emptied, followed by the addition of 50 μl/well of a pool of primate serum in two-fold dilution series starting from 1 in 100 dilution. The plate was incubated for 1 hour at RT and then washed five times with PBS+0.05% Tween (PBS-T). For detection, a goat anti human Ig-HRP antibody was used diluted 1/5000 (Southern Biotechnology). The plate was incubated for 50 min at RT followed by a five-times washing step using PBS-T. For color development, 50 μl of ImmunoPure TMB substrate (Pierce) were added and the plate was incubated in the dark at RT for 12 min. Color reaction was stopped by adding stop solution (2 M $H_2SO_4$) and the absorbance was measured at 450 nm.

Calculation of IVA-Values

The IVA ELISA was subsequently performed as described above. The resulting titration curves were plotted in a graph using a XY-non-linear regression formula to obtain a dilution value at OD 0.3. The standard dilution value at OD 0.3 was set to 100 and the IVA-value for each sample was calculated by relating it to the standard. Consequently, an IVA-value below 100 reflects a lower degree of primate Ig-binding of that particular HER2 specific polypeptide compared with the standard Z00342. Four different HER2 specific polypeptides were evaluated for in vitro antigenicity i.e. Affibody® molecules I, II, II with DOTA and XI with DOTA. These polypeptides were shown to have a low in vitro antigenicity profile compared with the standard protein. The conclusion is that he amino acid alterations that were made resulted in a decreased potential to interact with immunoglobulins.

TABLE 3

IVA-values of different HER2 specific polypeptides related to the standard Z00342.

| Affibody ® molecule | IVA-Value |
| --- | --- |
| Standard Z00342 | 100 |
| I | 13 |
| II | 4 |
| II with DOTA | 6 |
| XI with DOTA | 1 |

The invention claimed is:

1. A method of treatment of a mammalian, including human, subject having a cancer characterized by overexpression of HER2, comprising the step of administering a therapeutically effective amount of a radiolabeled polypeptide into the body of the subject, said radio labeled polypeptide comprising:
   (1) a HER2 binding polypeptide comprising the amino acid sequence EX$_1$RNAYWEIA LLPNLTNQQK RAFIRKLYDD PSQSSELLX$_2$E AKKLNDSQ wherein X$_1$ in position 2 is M, I or L, and X$_2$ in position 39 is S or C (SEQ ID NO:1), and
   (2) a radionuclide suitable for therapy.

2. The method according to claim 1, comprising, before the administration step, a step of preparing a radiolabeled polypeptide, comprising mixing said HER2 binding polypeptide with a suitable radionuclide.

3. The method according to claim 1, wherein the cancer is selected from breast cancer, ovarian cancer, stomach cancer, bladder cancer, salivary cancer, lung cancer and cancer in the esophagus.

4. The method according to claim 1, wherein said HER2 binding polypeptide comprises the amino acid sequence
   YAKEX$_1$RNAYW EIALLPNLTN QQKRAFIRKL YDDPSQSSEL LX$_2$EAKKLNDS Q wherein X$_1$ in position 5 is M, I or L, and X$_2$ in position 42 is S or C (SEQ ID NO:2).

5. The method according to claim 1, wherein said HER2 binding polypeptide comprises the amino acid sequence
   AEAKYAKEX$_1$R NAYWEIALLP NLTNQQKRAF IRKLYDDPSQ SSELLX$_2$EAKK LNDSQ wherein X$_1$ in position 9 is M, I or L, and X$_2$ in position 46 is S or C (SEQ ID NO:3).

6. The method according to claim 1, wherein said HER2 binding polypeptide comprises the amino acid sequence
   ESEKYAKEX$_1$R NAYWEIALLP NLTNQQKRAF IRKLYDDPSQ SSELLX$_2$EAKK LNDSQ wherein X$_1$ in position 9 is M, I or L, and X$_2$ in position 46 is S or C (SEQ ID NO:4).

7. The method according to claim 1, wherein said HER2 binding polypeptide comprises the amino acid sequence
   AEAKYAKEMR NAYWEIALLP NLTNQQKRAF IRKLYDDPSQ SSELLSEAKK LNDSQAPKVD C (SEQ ID NO:5).

8. The method according to claim 1, wherein said HER2 binding polypeptide comprises the amino acid sequence ESEKYAKEMR NAYWEIALLP NLTNQQKRAF IRKLYDDPSQ SSELLSEAKK LNDSQAPK (SEQ ID NO:6).

9. The method according to claim 1, wherein said HER2 binding polypeptide further comprises a mercaptoacetyl coupled to the N-terminal thereof, wherein a chelating environment constituted by a N$_3$S chelator motif is provided by the nitrogen atoms of the first three consecutive peptide bonds from the N-terminal, together with the SH group of the mercapto acetyl.

10. The method according to claim 9, wherein the first three consecutive peptide bonds from the N-terminal of said HER2 binding polypeptide are provided by the amino groups of residues ESE.

11. The method according to claim 1, wherein said HER2 binding polypeptide has the sequence maESEKYAKEMR NAYWEIALLP NLTNQQKRAF IRKLYDDPSQ SSELLSEAKK LNDSQAPK wherein ma is mercaptoacetyl (SEQ ID NO:7).

12. The method according to claim 1, wherein said HER2 binding polypeptide comprises a cysteine residue either already present in the sequence or as an additional amino acid residue or by replacing a surface exposed amino acid residue that is not involved in HER2 binding.

13. The method according to claim 12, wherein the cysteine residue of said HER2 binding polypeptide is the one situated at the C-terminal end of SEQ ID NO:5 or the additional cysteine is situated at the C-terminal of any of SEQ ID NO:1-4 or 6-7, wherein the cysteine residue optionally is followed by one or more other amino acid residue(s), and wherein a chelating environment is constituted by a N$_3$S chelator motif is provided by the nitrogen atoms of three consecutive peptide bonds in the stretch of amino acid resides constituted by the cysteine and the two preceding amino acid residues, together with the SH group of the cysteine residue.

14. The method according to claim 12, wherein said HER2 binding polypeptide comprises a chelating environment provided by a polyaminopolycarboxylate chelator coupled to the polypeptide via a thiol group.

15. The method according to claim 14, wherein the polyaminopolycarboxylate chelator of said HER2 binding polypeptide is 1,4,7,10-tetraazacyclododecane-1,4,7,10-tetraacetic acid or a derivative thereof.

16. The method according to claim 15, wherein the 1,4,7,10-tetraazacyclododecane-1,4,7,10-tetraacetic acid derivative is 1,4,7,10-tetraazacyclododecane-1,4,7-tris-acetic acid-10-maleimidoethylacetamide.

17. The method according to claim 1, wherein the HER2 binding polypeptide consists of SEQ ID NO:5 coupled to 1,4,7,10-tetraazacyclododecane-1,4,7-tris-acetic acid-10-maleimidoethylacetamide.

18. The method according to claim 14, wherein the polyaminopolycarboxylate chelator of said HER2 binding polypeptide is diethylenetriaminepentaacetic acid or derivatives thereof.

19. The method according to claim 9, wherein the radiolabeled polypeptide consists of a radiochelate of said HER2 binding polypeptide, and a radionuclide selected from the group consisting of $^{186}$Re and $^{188}$Re.

20. The method according to claim 13, wherein the radiolabeled polypeptide consists of a radiochelate of said HER2 binding polypeptide, and a radionuclide selected from the group consisting of $^{186}$Re and $^{188}$Re.

21. The method according to claim 14, wherein the radiolabeled polypeptide consists of a radiochelate of said HER2 binding polypeptide and a radionuclide selected from the group consisting of $^{225}$Ac, $^{212}$Bi, $^{213}$Bi, $^{67}$Cu, $^{166}$HO, $^{177}$Lu, $^{212}$Pb, $^{149}$Pm, $^{153}$Sm, $^{227}$Th and $^{90}$Y, wherein the radionuclide is complexed with the HER2 binding polypeptide via the chelating environment.

22. The method according to claim 12, wherein the radiolabeled polypeptide consists of said HER2 binding polypeptide linked via a linker molecule to a radionuclide selected from the group consisting of $^{211}$At, $^{76}$Br, $^{18}$F and iodine isotopes.

* * * * *

SEQUENCE LISTING

<160> NUMBER OF SEQ ID NOS: 7

<210> SEQ ID NO 1
<211> LENGTH: 48
<212> TYPE: PRT
<213> ORGANISM: Artificial Sequence
<220> FEATURE:
<223> OTHER INFORMATION: HER-2 Binding Polypeptide
<220> FEATURE:
<221> NAME/KEY: VARIANT
<222> LOCATION: 2
<223> OTHER INFORMATION: Xaa = M, I or L
<220> FEATURE:
<221> NAME/KEY: VARIANT
<222> LOCATION: 39
<223> OTHER INFORMATION: Xaa = S or C

<400> SEQUENCE: 1

Glu Xaa Arg Asn Ala Tyr Trp Glu Ile Ala Leu Leu Pro Asn Leu Thr
1               5                   10                  15

Asn Gln Gln Lys Arg Ala Phe Ile Arg Lys Leu Tyr Asp Asp Pro Ser
            20                  25                  30

Gln Ser Ser Glu Leu Leu Xaa Glu Ala Lys Lys Leu Asn Asp Ser Gln
        35                  40                  45

<210> SEQ ID NO 2
<211> LENGTH: 51
<212> TYPE: PRT
<213> ORGANISM: Artificial Sequence
<220> FEATURE:
<223> OTHER INFORMATION: HER-2 Binding Polypeptide
<220> FEATURE:
<221> NAME/KEY: VARIANT
<222> LOCATION: 5
<223> OTHER INFORMATION: Xaa = M, I, or L
<220> FEATURE:
<221> NAME/KEY: VARIANT
<222> LOCATION: 42
<223> OTHER INFORMATION: Xaa = S or C

<400> SEQUENCE: 2

Tyr Ala Lys Glu Xaa Arg Asn Ala Tyr Trp Glu Ile Ala Leu Leu Pro
1               5                   10                  15

Asn Leu Thr Asn Gln Gln Lys Arg Ala Phe Ile Arg Lys Leu Tyr Asp
            20                  25                  30

Asp Pro Ser Gln Ser Ser Glu Leu Leu Xaa Glu Ala Lys Lys Leu Asn
        35                  40                  45

Asp Ser Gln
        50

<210> SEQ ID NO 3
<211> LENGTH: 55
<212> TYPE: PRT
<213> ORGANISM: Artificial Sequence
<220> FEATURE:
<223> OTHER INFORMATION: HER-2 Binding Polypeptide
<220> FEATURE:
<221> NAME/KEY: VARIANT
<222> LOCATION: 9
<223> OTHER INFORMATION: Xaa = M, I, or L
<220> FEATURE:
<221> NAME/KEY: VARIANT
<222> LOCATION: 46
<223> OTHER INFORMATION: Xaa = S or C

<400> SEQUENCE: 3

Ala Glu Ala Lys Tyr Ala Lys Glu Xaa Arg Asn Ala Tyr Trp Glu Ile
1               5                   10                  15

-continued

```
Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Xaa Glu Ala
        35                  40                  45

Lys Lys Leu Asn Asp Ser Gln
    50                  55

<210> SEQ ID NO 4
<211> LENGTH: 55
<212> TYPE: PRT
<213> ORGANISM: Artificial Sequence
<220> FEATURE:
<223> OTHER INFORMATION: HER-2 Binding Polypeptide
<220> FEATURE:
<221> NAME/KEY: VARIANT
<222> LOCATION: 9
<223> OTHER INFORMATION: Xaa = M, I, or L
<220> FEATURE:
<221> NAME/KEY: VARIANT
<222> LOCATION: 46
<223> OTHER INFORMATION: Xaa = S or C

<400> SEQUENCE: 4

Glu Ser Glu Lys Tyr Ala Lys Glu Xaa Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Xaa Glu Ala
        35                  40                  45

Lys Lys Leu Asn Asp Ser Gln
    50                  55

<210> SEQ ID NO 5
<211> LENGTH: 61
<212> TYPE: PRT
<213> ORGANISM: Artificial Sequence
<220> FEATURE:
<223> OTHER INFORMATION: HER-2 Binding Polypeptide

<400> SEQUENCE: 5

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60

<210> SEQ ID NO 6
<211> LENGTH: 58
<212> TYPE: PRT
<213> ORGANISM: Artificial Sequence
<220> FEATURE:
<223> OTHER INFORMATION: HER-2 Binding Polypeptide

<400> SEQUENCE: 6

Glu Ser Glu Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
```

```
                35                  40                  45
Lys Lys Leu Asn Asp Ser Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: HER-2 Binding Polypeptide
<220> FEATURE:
<221> NAME/KEY: ACETYLATION
<222> LOCATION: 1
<223> OTHER INFORMATION: The sequence comprises a mercaptoacetyl group
      (ma) coupled to the N-terminal

<400> SEQUENCE: 7

Glu Ser Glu Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys
    50                  55
```